US010480104B2

(12) United States Patent
Fu et al.

(10) Patent No.: US 10,480,104 B2
(45) Date of Patent: Nov. 19, 2019

(54) SMART YARN AND METHOD FOR MANUFACTURING A YARN CONTAINING AN ELECTRONIC DEVICE

(71) Applicant: Siren Care, Inc., San Francisco, CA (US)

(72) Inventors: Jie Fu, Shanghai (CN); Ran Ma, San Francisco, CA (US); Henk Jan Scholten, The Hague (NL)

(73) Assignee: SIREN CARE, INC., San Francisco, CA (US)

( * ) Notice: Subject to any disclaimer, the term of this patent is extended or adjusted under 35 U.S.C. 154(b) by 287 days.

(21) Appl. No.: 15/717,498

(22) Filed: Sep. 27, 2017

(65) Prior Publication Data

US 2018/0087193 A1 Mar. 29, 2018

Related U.S. Application Data

(60) Provisional application No. 62/400,436, filed on Sep. 27, 2016.

(51) Int. Cl.
*D02G 3/44* (2006.01)
*A61B 5/00* (2006.01)
(Continued)

(52) U.S. Cl.
CPC .............. *D02G 3/441* (2013.01); *A61B 5/01* (2013.01); *A61B 5/6807* (2013.01); *A61B 5/742* (2013.01);
(Continued)

(58) Field of Classification Search
CPC ................. H05K 1/0393; H05K 3/284; H05K 2201/10106; H05K 2201/10151;
(Continued)

(56) References Cited

U.S. PATENT DOCUMENTS

| 4,670,977 A | 6/1987 | Scrantom et al. |
| 5,191,895 A | 3/1993 | Koltringer |

(Continued)

FOREIGN PATENT DOCUMENTS

| EP | 2 591 717 B1 | 8/2016 |
| GB | 2472025 A | 1/2011 |

(Continued)

OTHER PUBLICATIONS

Hughes-Riley. "A Study of Thermistor Performance within a Textile Structure", Jul. 5, 2017 (Year: 2017).*

(Continued)

*Primary Examiner* — Peter Dungba Vo
*Assistant Examiner* — Joshua D Anderson
(74) *Attorney, Agent, or Firm* — Cooley LLP

(57) ABSTRACT

Once variation of a method for producing a smart yarn includes: advancing a set of wires into an assembly field; at each sensor site in a series of sensor sites along the set of wires, depositing solder paste onto the set of wires at the sensor site, placing a sensor into the solder paste on the set of wires at the sensor site, and heating the set of wires within the assembly field to reflow the solder paste; wrapping fibers around the set of wires and sensors arranged along the set of wires to form a continuous length of the smart yarn; separating a first segment of the smart yarn from the continuous length of the smart yarn; and weaving the first segment of the smart yarn into a garment.

20 Claims, 11 Drawing Sheets

(51) Int. Cl.
| | |
|---|---|
| *A61B 5/01* | (2006.01) |
| *D03D 1/00* | (2006.01) |
| *D04B 1/24* | (2006.01) |
| *H05K 1/03* | (2006.01) |
| *H05K 1/18* | (2006.01) |
| *H05K 3/34* | (2006.01) |
| *D04B 1/26* | (2006.01) |
| *A41D 1/00* | (2018.01) |
| *H05K 3/28* | (2006.01) |

(52) U.S. Cl.
CPC .............. *D02G 3/44* (2013.01); *D03D 1/0088* (2013.01); *D04B 1/24* (2013.01); *D04B 1/26* (2013.01); *H05K 1/181* (2013.01); *A41D 1/005* (2013.01); *A61B 2560/0209* (2013.01); *A61B 2560/0242* (2013.01); *A61B 2562/029* (2013.01); *A61B 2562/0219* (2013.01); *A61B 2562/0247* (2013.01); *A61B 2562/0257* (2013.01); *A61B 2562/04* (2013.01); *A61B 2562/125* (2013.01); *D10B 2401/18* (2013.01); *D10B 2403/02431* (2013.01); *D10B 2501/043* (2013.01); *H05K 1/0393* (2013.01); *H05K 3/284* (2013.01); *H05K 3/3415* (2013.01); *H05K 2201/029* (2013.01); *H05K 2201/10106* (2013.01); *H05K 2201/10151* (2013.01)

(58) Field of Classification Search
CPC .............. H05K 2201/029; D02G 3/441; D03D 1/0088; A61B 5/6807; A61B 5/01; A61B 2560/0242; A61B 2560/04; A61B 2560/12; A61B 2560/125; A41D 1/005; D10B 2401/18; D10B 2403/02431; D10B 2501/043; Y10T 29/49002; Y10T 29/49169; Y10T 29/49171; Y10T 29/49179; Y10T 29/5313; Y10T 29/53213
See application file for complete search history.

(56) References Cited

U.S. PATENT DOCUMENTS

| | | | |
|---|---|---|---|
| 5,446,452 A | 8/1995 | Litton | |
| 5,546,955 A | 8/1996 | Wilk | |
| 5,642,096 A | 6/1997 | Leyerer et al. | |
| 5,678,566 A | 10/1997 | Dribbon | |
| 5,788,114 A | 8/1998 | Perego | |
| 5,929,332 A | 7/1999 | Brown | |
| 6,398,740 B1 | 6/2002 | Lavery et al. | |
| 7,716,005 B2 | 5/2010 | Shoureshi et al. | |
| 8,360,987 B2 | 1/2013 | Kantro et al. | |
| 8,536,075 B2 | 9/2013 | Leonard | |
| 10,301,751 B2 | 5/2019 | Dias et al. | |
| 2002/0082486 A1 | 6/2002 | Lavery et al. | |
| 2004/0009729 A1 | 1/2004 | Hill et al. | |
| 2005/0070778 A1 | 3/2005 | Lackey et al. | |
| 2007/0194130 A1* | 8/2007 | Bauer | G06K 19/07749 235/492 |
| 2009/0139198 A1 | 6/2009 | Dias et al. | |
| 2010/0324455 A1 | 12/2010 | Rangel et al. | |
| 2012/0109013 A1 | 5/2012 | Everett et al. | |
| 2013/0092742 A1 | 4/2013 | Brun et al. | |
| 2013/0137943 A1 | 5/2013 | Rodrigues | |
| 2013/0145588 A1* | 6/2013 | Nakata | D03D 1/0076 29/25.01 |
| 2013/0192071 A1 | 8/2013 | Esposito et al. | |
| 2013/0213147 A1 | 8/2013 | Rice et al. | |
| 2013/0261494 A1 | 10/2013 | Bloom et al. | |
| 2015/0057562 A1 | 2/2015 | Linders et al. | |
| 2015/0157263 A1 | 6/2015 | Workman et al. | |
| 2015/0173679 A1 | 6/2015 | West et al. | |
| 2015/0177080 A1 | 6/2015 | Esposito et al. | |
| 2015/0190059 A1 | 7/2015 | Petersen et al. | |
| 2015/0297100 A1 | 10/2015 | Castillo | |
| 2016/0256706 A1 | 9/2016 | Harrison | |
| 2017/0188841 A1 | 7/2017 | Ma et al. | |
| 2017/0275789 A1 | 9/2017 | Dias et al. | |
| 2017/0333256 A1 | 11/2017 | Bassez et al. | |
| 2018/0087192 A1 | 3/2018 | Fu et al. | |
| 2019/0117080 A1 | 4/2019 | Ma et al. | |

FOREIGN PATENT DOCUMENTS

| | | | |
|---|---|---|---|
| WO | WO-02/095839 A2 | 11/2002 | |
| WO | WO-02/095839 A3 | 11/2002 | |
| WO | WO-2008/080245 A2 | 7/2008 | |
| WO | WO-2008/080245 A3 | 7/2008 | |
| WO | WO-2009/005373 A1 | 1/2009 | |
| WO | 2011010093 A1 | 1/2011 | |
| WO | WO-2011010093 A1 * | 1/2011 | ............. D02G 3/441 |
| WO | 2016038342 A1 | 3/2016 | |
| WO | WO-2016038342 A1 * | 3/2016 | ............... D02G 3/36 |
| WO | WO-2017/106760 A1 | 6/2017 | |
| WO | 2017115083 A1 | 7/2017 | |
| WO | WO-2017/120063 A1 | 7/2017 | |
| WO | WO-2017115083 A1 * | 7/2017 | ............. D02G 3/441 |
| WO | 2017175001 A1 | 10/2017 | |
| WO | WO-2017175001 A1 * | 10/2017 | ............. D02G 3/441 |
| WO | WO-2018/064174 A1 | 4/2018 | |

OTHER PUBLICATIONS

Hardy, D. A. et al. (2019) "Automated Insertion of Package Dies onto Wire and into a Textile Yarn Sheath" (Year: 2019).*
Nashed, M-N. et al. (2019) A Novel Method for Embedding Semiconductor Dies within Textile Yarn to Create Electronic Textiles (Year: 2019).*
Hughes-Riley. "A Study of Thermistor Performance within a Textile Structure." Jul. 5, 2017 (Jul. 5, 2017) Retrieved from < http://www.mdpi.com/1424-8220/17/8/1804 > entire document.
Hardy, D.A. et al. (2019). "Automated insertion of package dies onto wire and into a textile yarn sheath," Microsystem Technologies, pp. 1-13.
Nashed, M-N. et al. (2019). "A novel method for embedding semiconductor dies within textile yarn to create electronic textiles," Fibers 7:12, 17 total pages.
Extended European Search Report dated Apr. 9, 2019, for EP Application No. 16 876 847.1, filed on Dec. 16, 2016, 11 pages.
International Search Report dated Mar. 27, 2017, for PCT Application No. PCT/US2016/067344, filed on Dec. 16, 2016, 3 pages.
International Search Report dated Feb. 6, 2018, for PCT Application No. PCT/US2017/053738, filed on Sep. 27, 2017, 4 pages.
International Search Report dated May 1, 2019, for PCT Application No. PCT/US2019/018714, filed on Feb. 20, 2019, 2 pages.
Non-Final Office Action dated Mar. 4, 2019, for U.S. Appl. No. 16/221,340, filed Dec. 14, 2018, 17 pages.
Notice of Allowance dated May 30, 2019, for U.S. Appl. No. 15/717,473, filed Sep. 27, 2017, 9 pages.
Written Opinion of the International Searching Authority dated Mar. 27, 2017, for PCT Application No. PCT/US2016/067344, filed on Dec. 16, 2016, 8 pages.
Written Opinion of the International Searching Authority dated Feb. 6, 2018, for PCT Application No. PCT/US2017/053738, filed on Sep. 27, 2017, 10 pages.
Written Opinion of the International Searching Authority dated May 1, 2019, for PCT Application No. PCT/US2019/018714, filed on Feb. 20, 2019, 4 pages.

* cited by examiner

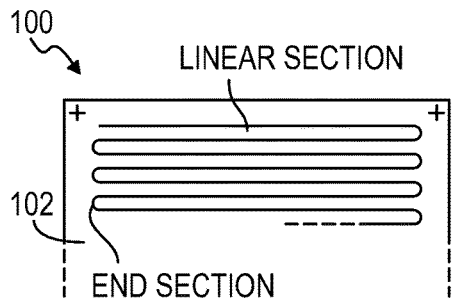
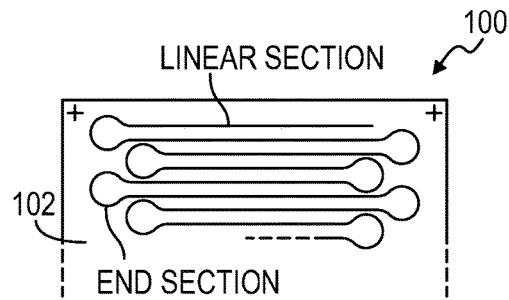
*FIG. 3A*  *FIG. 3B*
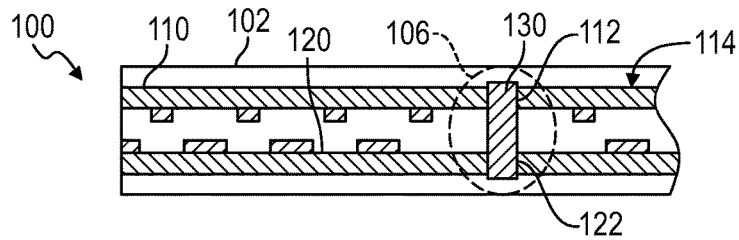
*FIG. 4A*
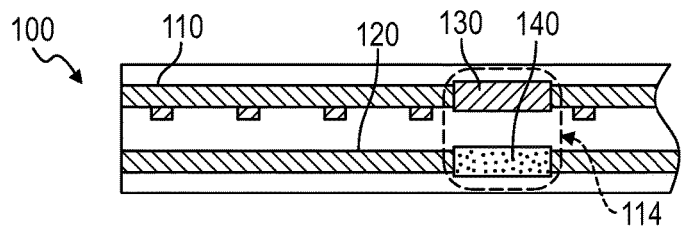
*FIG. 4B*
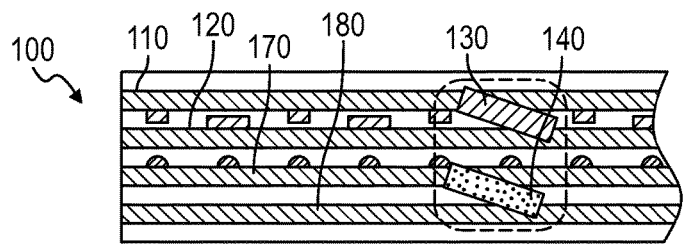
*FIG. 4C*
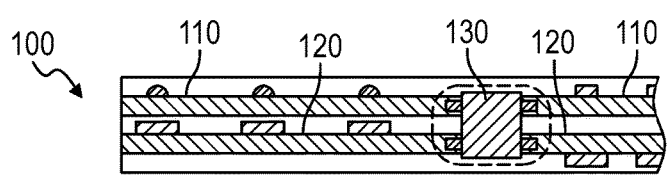
*FIG. 4D*

SMART YARN AND METHOD FOR MANUFACTURING A YARN CONTAINING AN ELECTRONIC DEVICE

CROSS-REFERENCE TO RELATED APPLICATIONS

This Application claims the benefit of U.S. Provisional Application No. 62/400,436, filed on 27 Sep. 2016, which is incorporated in its entirety by this reference.

The application is related to U.S. patent application Ser. No. 15/382,248, filed on 16 Dec. 2016, which is incorporated in its entirety by this reference.

TECHNICAL FIELD

This invention relates generally to the field of smart textiles and more specifically to a new and useful smart yarn and method for manufacturing a yarn containing an electronic device in the field of smart textiles.

BRIEF DESCRIPTION OF THE FIGURES

FIGS. 3A and 3B are schematic representations of variations of the smart yarn;
FIGS. 4A-4D are schematic representations of variations of the smart yarn.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First Method: Smart Yarn

Figure 1:
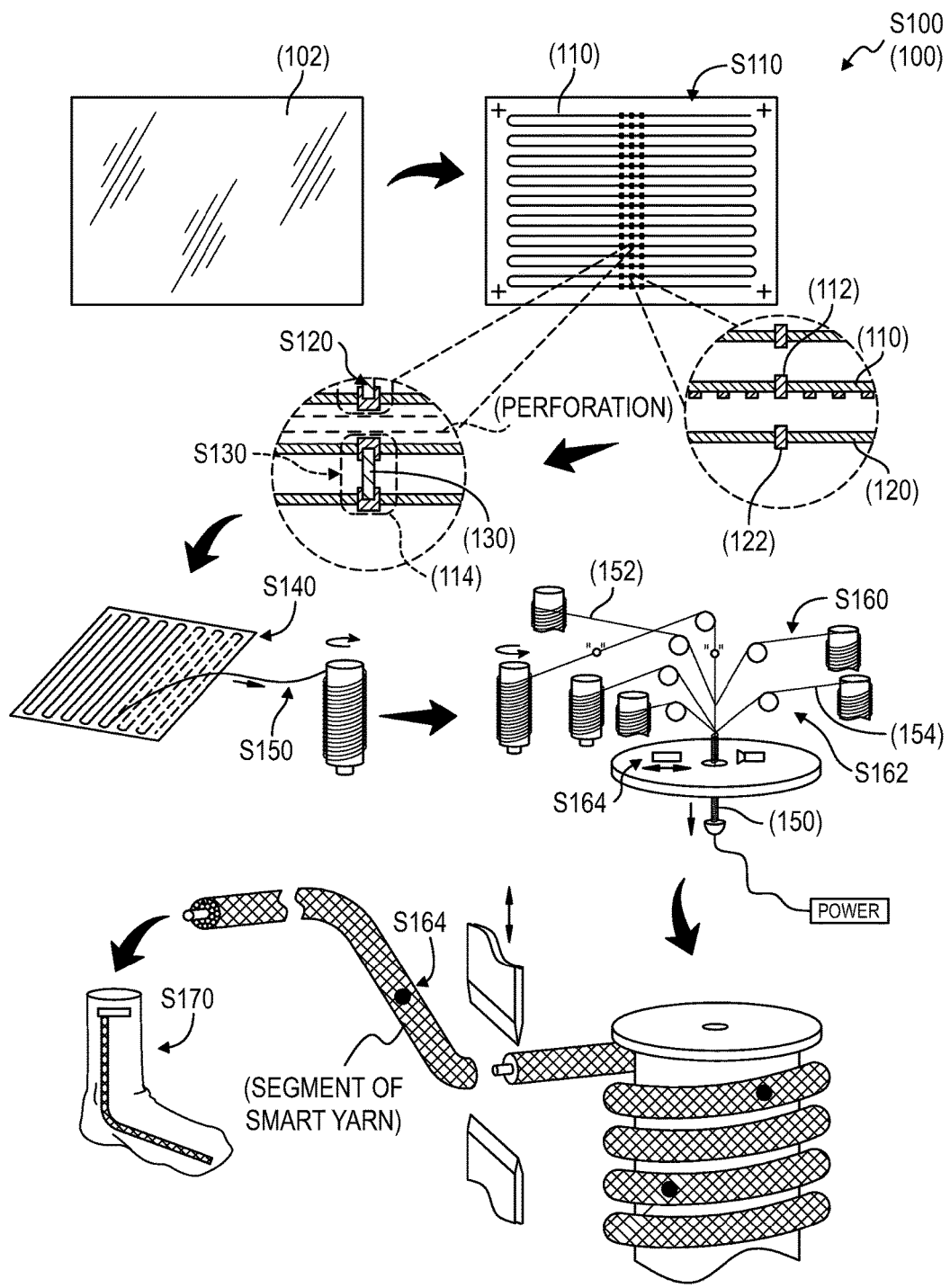
FIG. 1 is a flowchart representation of a first method.
Figure 2:
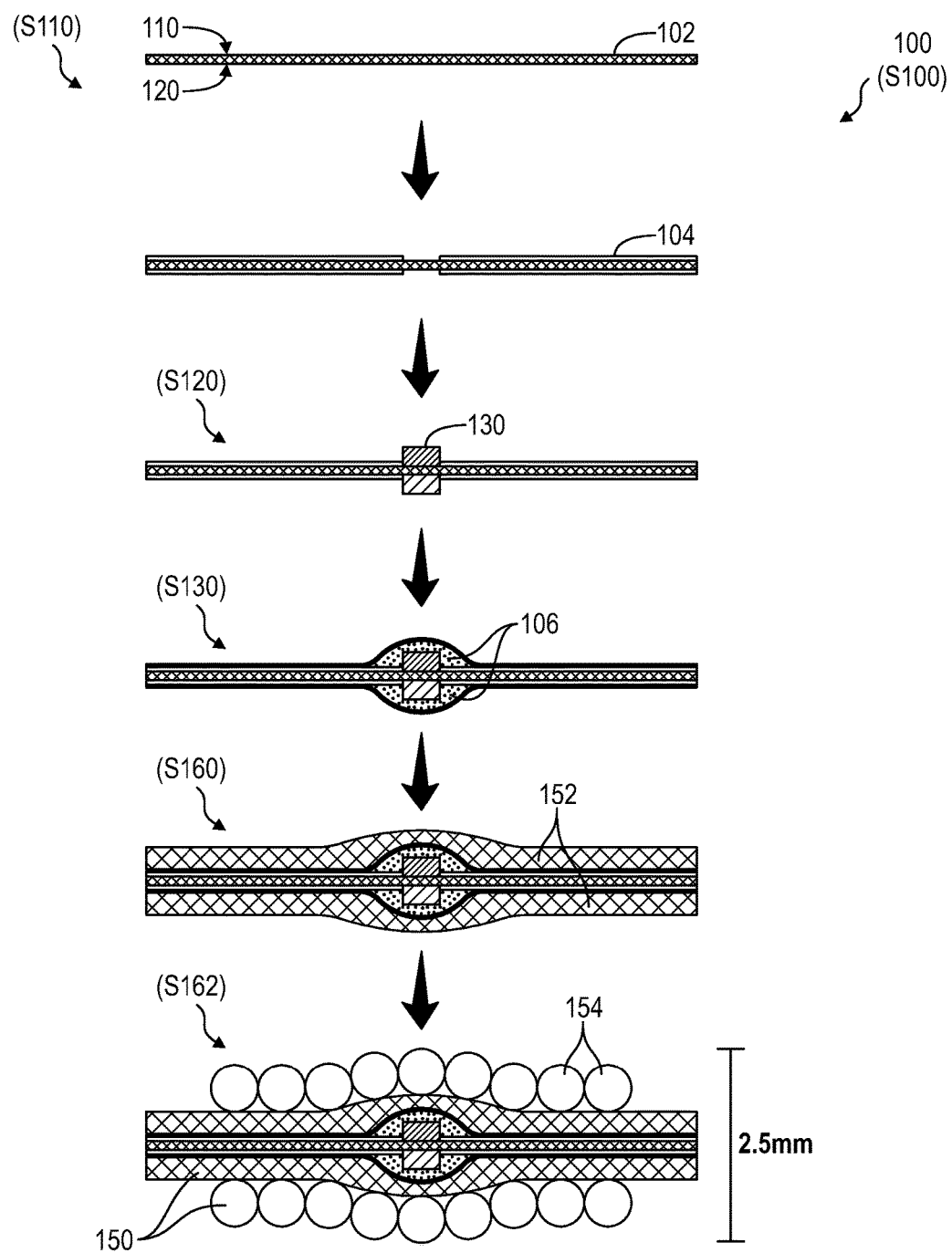
FIG. 2 is a flowchart representation of a smart yarn.

As shown in FIGS. 1 and 2, a smart yarn 100 includes: a flexible substrate 102; a first trace no extending from a first end of the flexible substrate 102 to a second end of the flexible substrate 102 and defining a first set of trace pads 112 at a component site 114; a second trace 120 extending from the first end of the flexible substrate 102 to the second end of the flexible substrate 102 and defining a second set of trace pads 122 at the component site 114; a sensor 130 coupled to the first set of trace pads 112 at the component site 114; a light element 140 coupled to the second set of trace pads 122 at the component site 114; and a textile sleeve 150 including packing fibers 152 arranged axially along the flexible substrate 102 and over the sensor 130 and the light element 140 and wrapping fibers 154 wrapped radially over the packing fibers 152 along the flexible substrate 102. The light element 140 is configured to output light when powered via the second trace 120 to visually indicate a location of the component site 114 along the flexible substrate 102.

One variation of the smart yarn 100 includes: a flexible substrate 102; a first trace 110 extending from a first end of the flexible substrate 102 to a second end of the flexible substrate 102, defining a set of component sites 114 distributed along a length of the flexible substrate 102, and defining a first set of trace pads 112 at each component site 114 in the set of component sites 114; a second trace 120 extending from the first end of the flexible substrate 102 to the second end of the flexible substrate 102 and defining a second set of trace pads 122 at each component site 114 in the set of component sites 114; a set of sensors, each sensor in the set of sensors coupled to a first set of trace pads 112 at a component site 114 in the set of component sites 114; a set of light elements 140, each light element 140 in the set of light elements 140 coupled to a second set of trace pads 122 at a component site 114 in the set of component sites 114; and a textile sleeve 150 including packing fibers 152 arranged axially along the flexible substrate 102 and over the set of sensors and the set of light elements 140 and wrapping fibers 154 wrapped radially over the packing fibers 152 along the flexible substrate 102.

1.1 First Method

As shown in FIG. 1, a first method S100 for manufacturing a yarn containing an electronic device includes: etching a serpentine trace onto a flexible substrate 102 in Block S102, the serpentine trace defining a set of parallel linear sections and a set of end sections coupling adjacent ends of linear sections in the set of parallel linear sections; installing an electrical component at a component site 114 on a linear section in the set of parallel linear sections in Block S120; applying sealant 106 between the electrical component and the flexible substrate 102 in Block S130; removing regions of the flexible substrate 102 beyond the serpentine trace to form a flexible serpentine circuit board in Block S140; deforming a first end section in the set of end sections interposed between a first linear section and a second linear section in the set of parallel linear sections to substantially axially align the first linear section and the second linear section in Block S150; arranging packing fibers 152 axially along the first linear section, the first end section, and the second end section in Block S160; wrapping the packing fibers 152 with wrapping fibers 154 to form a length of smart yarn in Block S162; and weaving a section of the length of smart yarn into a garment in Block S170.

1.2 Applications

Generally, the length of smart yarn 100 contains (a portion of) an electrical circuit wrapped in a textile sleeve 150 and can be woven into a garment or combined with other fiber strands to form a garment. In particular, the length of smart yarn 100 includes a serpentine electrical circuit: defining straight sections and end sections connecting ends of adjacent straight sections; including electrical traces and electrical components; cut from a flexible substrate 102 of limited length and width; and straightened by deforming its end sections to achieve an axial length significantly greater than the length and width of the flexible substrate 102; and wrapped in packing and wrapping fibers 154. The length of smart yarn 100 can thus define a soft, flexible and robust yarn strand including one or more actuators (e.g., a light-emitting diode, or "LED") and/or one or more sensors (e.g., a temperature sensor) that can be powered or sampled, respectively, to add additional "smart" functionality to a garment incorporating all or a section of the length of smart yarn 100.

Figure 11:
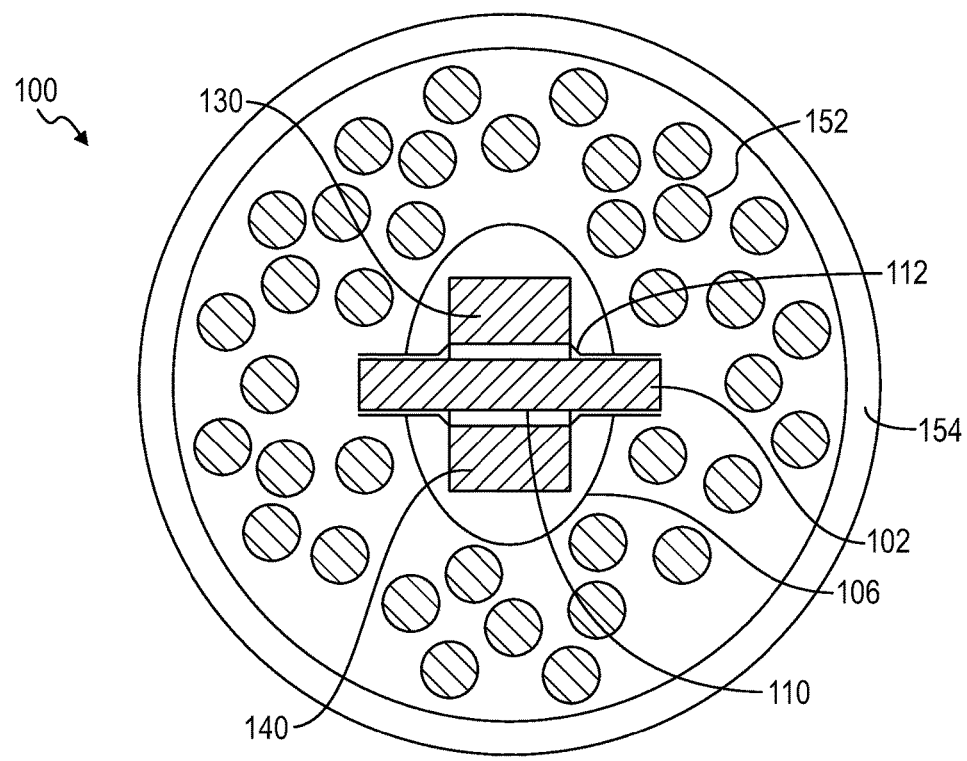
FIG. 11 is a schematic representation of one variation of the smart yarn.

The smart yarn can define a substantially uniform cross-sectional area along its length, including from a section of the smart yarn intersecting a trace on the flexible substrate 102 to a section on the smart yarn intersecting an electrical component, as shown in FIG. 11. The cross-section of the circuit board may be relatively small, and the textile sleeve 150 may be of a relative thickness and flexibility sufficient to tactilely and visually obscure the location of an electrical component along the length of the smart yarn. Therefore, when integrated into a garment (e.g., a "smart garment"), such as a sock or sweater, a user may not be able to feel an electrical component within the smart garment with her fingers or see the location of the electrical component within the smart garment with her eyes. A smart garment incorporating a section of the smart yarn can therefore be worn by the user without causing significant physical discomfort due to small, hard elements (e.g., a sensor) pressing against the user's skin, and the smart garment can discreetly measure a signal (e.g., the temperature of one region of the user's skin) via a sensor integrated into the smart yarn while the user wears the smart garment.

Figure 6:
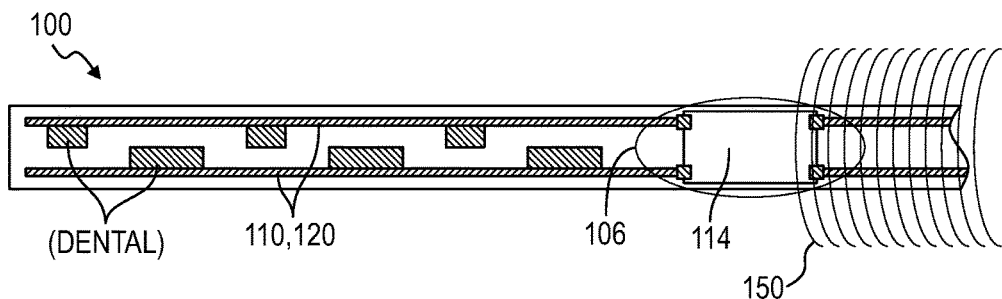
FIG. 6 is a schematic representation of one variation of the smart yarn.
Figure 7:
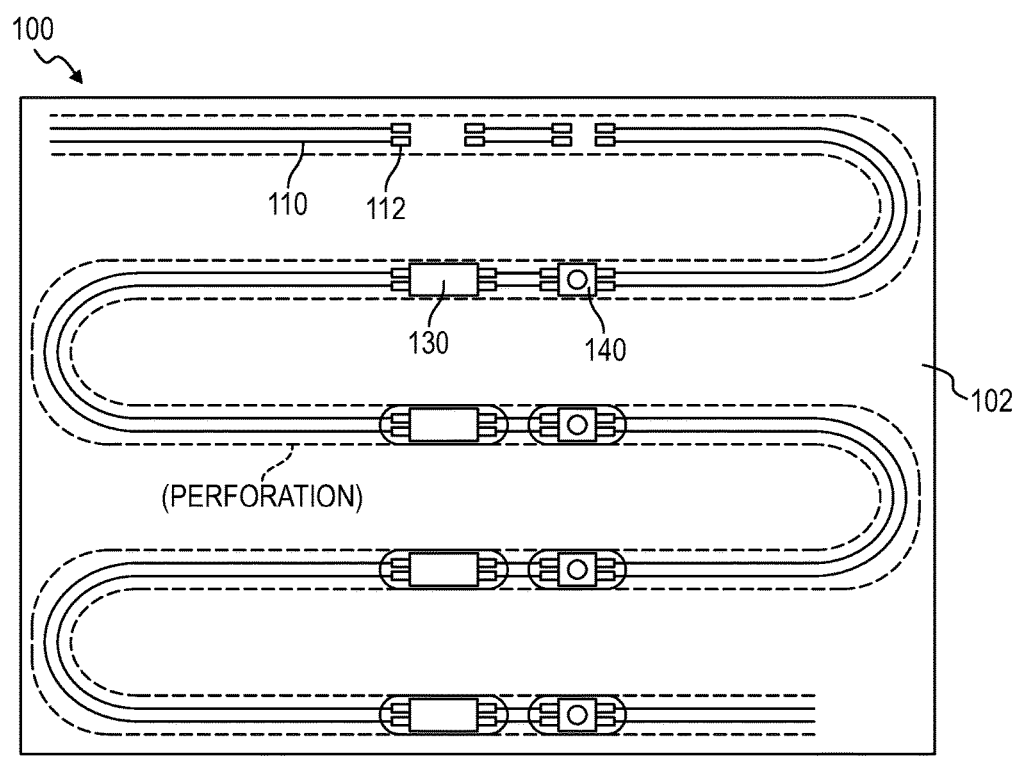
FIG. 7 is a schematic representation of one variation of the smart yarn.
Figure 8:
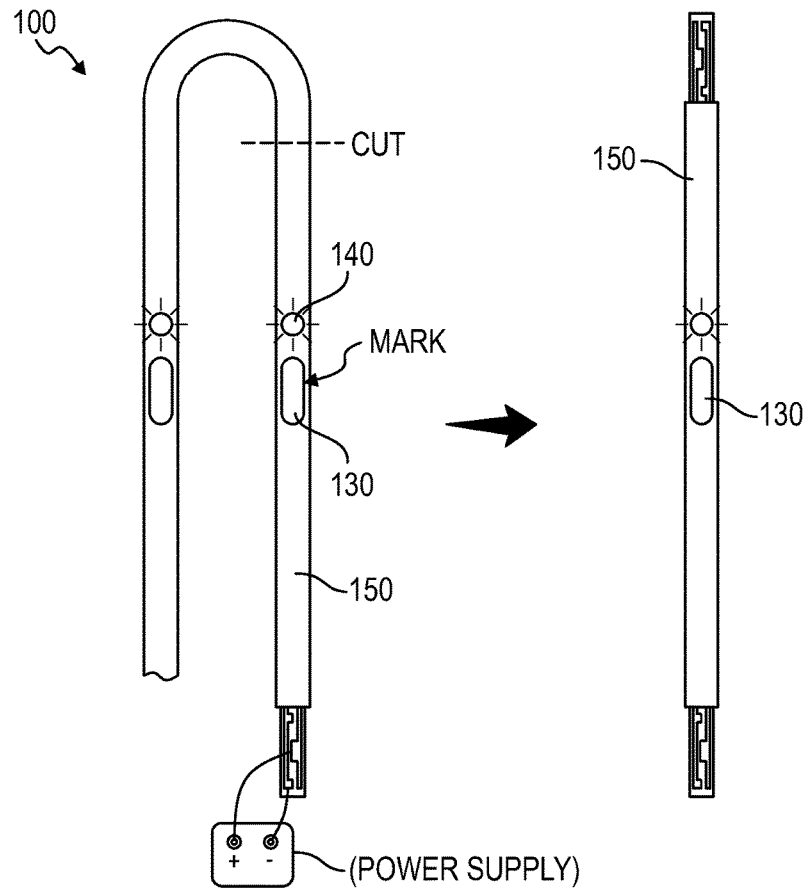
FIG. 8 is a flowchart representation of one variation of the smart yarn.
Figure 9:
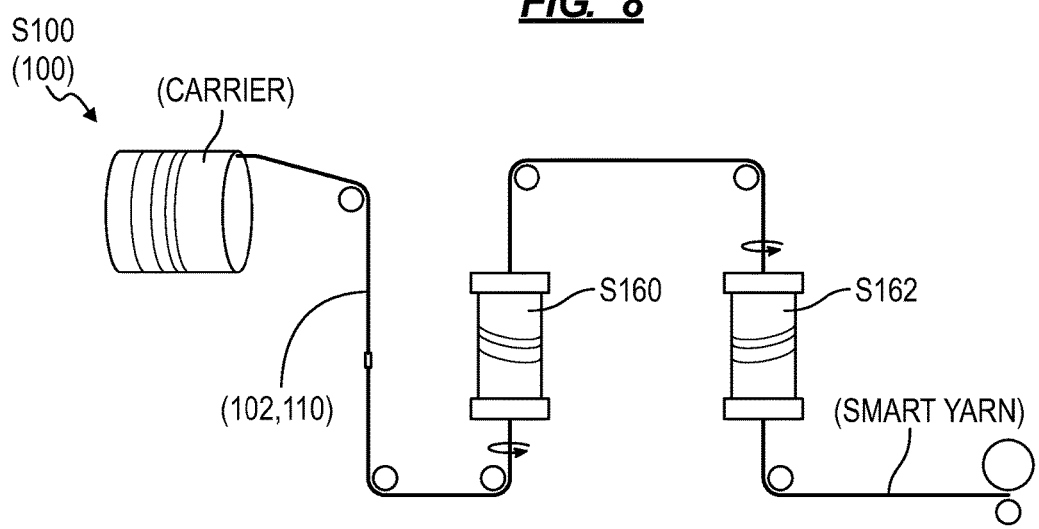
FIG. 9 is a flowchart representation of one variation of the first method yarn.

However, once the circuit board is wrapped with the textile sleeve 150, the location of a sensor along the length of the circuit board may be visually and tactilely obscured and therefore not immediately detectable by a human or machine. The smart yarn can therefore also include an actuator paired with each sensor. For example and as described below: the flexible substrate 102 can define a first trace no of a first circuit on its first side and a second trace 120 of a second circuit on its second side; the sensor 130 (e.g., a thermistor) can be arranged over the first trace no at a component site 114 on the first side of the flexible substrate 102; and the actuator can include an LED arranged over the second trace 120 at the same component site 114 on the second side of the flexible substrate 102 such that the LED and the sensor 130 fall within the same cross-section of the smart yarn. An LED and a sensor can be arranged directly over one another at a component site 114, as shown in FIG. 2. Alternatively, the LED and the sensor 130 can be offset along the length of the trace, as shown in FIG. 6, in order to minimize a difference between a smallest cross-section and a largest cross-section of the completed length of smart yarn 100. Once the flexible substrate 102, sensor, and actuator are wrapped in the textile sleeve 150 and thus obscured, the second trace 120 can be connected to a power supply in order to illuminate the LED, thereby lighting a local region of the smart yarn and visually indicating the position of both the LED and the adjacent sensor along the length of the smart yarn.

In the foregoing example, a machine can implement a light sensor or computer vision techniques to detect the illuminated LED and can physically mark the location of the LED—and therefore the sensor 130—on the exterior surface of the woven fibers, such as with chalk, ink, or paint. Alternatively, the machine can store the location of the LED and sensor virtually, such as by storing of a physical distance of the LED—relative a reference end of the length of smart yarn 100—in a virtual lookup table or in the form of a virtual model of the length of smart yarn 100 including a specification for the position of the LED and sensor. A garment knitting or weaving machine can then automatically assemble a garment with the length of smart yarn 100 based on the known location of the LED and sensor relative to the reference end of the length of smart yarn 100 such that the sensor 130 is arranged in a particular, target position of the garment upon its completion. Alternatively, a human operator can manually mark the position of an LED and its sensor pair while power is supplied to the LED(s) via the second trace 120, and a human operator can manually incorporate a section of smart yarn into a garment once the location of each LED and its sensor pair is thus identified.

The length of smart yarn 100 can include multiple sensors connected to a first circuit arranged along one contiguous section of flexible substrate 102 with each sensor paired with an LED connected to a second circuit arranged along the same section of the flexible substrate 102. Once the flexible substrate 102, sensors, and LEDs are wrapped with the textile sleeve 150 to form one contiguous length of smart yarn 100 containing multiple sensors, the second circuit can be coupled to a power supply in order to illuminate each LED, thereby indicating the position of each sensor along the section of smart yarn. The full length of smart yarn 100 can then be woven into one garment according to a weave pattern based on locations of sensors detected via the illuminated set of LEDs in order to achieve a particular, predefined arrangement of sensors across the garment. Alternatively, the length of smart yarn 100 can be cut in multiple discrete sections—each including one or more sensor and LED pairs—and each section of smart yarn can then be woven into a single garment or separated and woven into multiple discrete garments.

The first method S100 can thus be executed to create a length of smart yarn 100 and to incorporate a section of the smart yarn into a garment. For example, select Blocks of the first method S100 can be executed automatically by traditional printed circuit board ("PCB") surface mount technology ("SMT") processing equipment or by traditional low-temperature soldering processing equipment to complete a serpentine circuit board. Similarly, other Blocks of the first method S100 can be executed automatically by a traditional yarn-processing machine or other traditional textile production machine to wrap the circuit board with packing and wrapping fibers 154. Furthermore, other Blocks of the first method S100 can be executed automatically by a traditional garment production machine to weave a section of smart yarn into a garment, such as a sock or sweater, substantially without human handling. However, the Blocks of the first method S100 can be executed by any number of machines executing processes of any other type.

Furthermore, the smart yarn 100 is described below as including a series of temperature sensors and manufactured for incorporation into a sock, such as a temperature-sensing-enabled sock as described in U.S. patent application Ser. No. 15/382,248. However, all or a section of the length of smart yarn 100 can be similarly incorporated into: a floor covering (e.g., a rug, a carpet); a shoe; bedding materials (e.g., a pillow case, a bed sheets); a window dressing (e.g., drapes); a body or hand towel; or furniture upholstery (e.g., an upholstery fabric); etc. and can include any other type of sensor, such as pressure sensors, moisture sensors, ambient light sensors, etc.

1.3 Example

In one example, a section of smart yarn containing a temperature sensor is woven into a sock to enable temperature measurement of a user's foot while the user wears the sock. In this example, an end of the section of smart yarn can be connected to a wireless transmitter also integrated into the sock, such as mounted onto a flexible substrate 102 at a component site 114 in another section of smart yarn. The wireless transmitter can regularly sample the temperature sensor, such as once per minute, and can broadcast a temperature value read from the temperature sensor to a connected computing device, such as the user's smartphone. In this example, the sock can be provided to a diabetic to monitor foot health based on skin temperature, such as to detect local infection on the user's foot.

However, one or more sections of smart yarn can be integrated into a garment of any other type in any other way.

1.4 Flexible Substrate

The smart yarn includes flexible substrate 102. Generally, the flexible substrate 102 includes a flexible circuit board substrate, such as a flexible PCB of aramid fibers or other plastic, on which traces are fabricated (e.g., subtractively etched or additively printed) and electrical components placed before a serpentine section of the flexible substrate 102 is cut around the traces and electrical components in Block S140, straightened in Block S150, and wrapped in the textile sleeve 150 in Blocks S160 and S162.

In one implementation, the flexible substrate 102 defines a rectangular PCB sheet coated with a conductive material of a size: accepted by an automated PCB processing machine to etch the conductive coating on the PCB sheet to form one or more traces on the PCB sheet in Block S102; and accepted by an automated surface mount technology "pick and place" machine to place electrical components on the PCB sheet. For example, the flexible substrate 102 can define a rectangular PCB sheet 500 millimeters wide by 250 millimeters long and coated with copper on one or both sides. The maximum dimension of the flexible substrate 102 can therefore be less than one meter. However, by etching a serpentine trace into the layer of conductive material and cutting the flexible substrate 102 along the serpentine traces to form a serpentine circuit board in Blocks S120 and S140, the serpentine circuit board can be straightened in Block S150 to form a substantially straight, flexible circuit board many meters in length. Once wrapped with the textile sleeve 150 in Blocks S160 and S162, the completed length of smart yarn 100 can similarly be many meters in length.

1.5 Traces

The length of smart yarn 100 includes: a first trace 110 extending from a first end of the flexible substrate 102 to a second end of the flexible substrate 102 and defining a first set of trace pads 112 at a component site 114; and a second trace 120 extending from the first end of the flexible substrate 102 to the second end of the flexible substrate 102 and defining a second set of trace pads 122 at the component site 114. Generally, the length of smart yarn 100 includes one or more traces defining serpentine paths etched, deposited (e.g., "printed"), or otherwise applied onto one or both sides of the flexible substrate 102.

A trace formed across the flexible substrate 102 can define a serpentine path including multiple parallel linear sections spanning a large portion of the width of the flexible substrate 102 sheet. Each linear section of the serpentine trace can terminate on a first end in a curvilinear section connected to the end of the linear section above (except the first linear section) and can terminate on a second end in another curvilinear section connected to the end of the linear section below (except the last linear section), or vice versa. Each end section can define a straight section formed at 90° to its adjacent linear sections such that the trace forms a boustrophedonic path. Alternatively, each end section can define a semicircular path with all end sections characterized by the same radius. Yet alternatively, the trace can include nested curvilinear end sections, as shown in FIG. 3B, exhibiting larger radii, which may increase tear resistance across each end section when the end sections are deformed in Block S150 to straighten the serpentine circuit board. However, the trace can include end sections of any other form to connect the set of linear sections into one continuous path broken only by trace pads at each component site 114 along the trace.

Therefore, once the flexible substrate 102 is cut on each side of the trace in Block S140 to free the serpentine circuit board from waste material, the serpentine circuit board can be tensioned across its ends in Block S150 to straighten the serpentine circuit board into a substantially straight circuit board over its entire length. The straightened circuit can then be wrapped with packing and wrapping fibers 154 in Blocks S160 and S162, as described below. In particular, though the maximum working dimension of the rectangular flexible substrate 102 sheet may be relatively small, such as limited by PCB processing or SMT processing equipment, a serpentine trace can be formed on the flexible substrate 102 in Block S102, the flexible substrate 102 can be cut around the serpentine trace to form a serpentine circuit board in Block S140, and the serpentine circuit board can be straightened in Block S150 before or as it is wrapped in fibers in Blocks S160 and S162 in order to form a substantially straight length of smart yarn 100 of length significantly greater than the maximum working dimension of the original rectangular flexible substrate 102 sheet. For example, for a flexible substrate 102 that measures 500 millimeters wide and 250 millimeters long, the flexible substrate 102 can be cut into a single serpentine circuit board 1.0 millimeter wide with a pitch distance of 4.0 millimeters between linear sections of the serpentine circuit board and with semi-circular end sections of 2.0 millimeter radii connecting adjacent ends of the linear sections. In this example, when straightened, the serpentine circuit board can span a maximum length of approximately 30 meters with approximately 62% of the rectangular flexible substrate 102 sheet discarded as waste.

The smart yarn can also include a pair of parallel and offset (or "nested") traces on one side of the flexible substrate 102, as shown in FIGS. 1 and 4A. In one implementation, the smart yarn includes a pair of parallel traces on one side of the flexible PCB, wherein each trace extends fully across and defines one trace pad per component site 114. In this implementation, at each component site 114 on the flexible substrate 102, the anode side of an LED can be soldered to a trace pad on the first trace 110 at the component site 114, and the cathode side of the LED can be soldered to a trace pad on the second trace 120 at the component site 114, as shown in FIG. 4A, such that all LEDs at all component sites 114 on the flexible substrate 102 can be connected in parallel. Once the smart yarn is completed in Block S162, the first and second traces 110, 120 can be exposed at one end of the smart yarn and then connected to a power supply to illuminate all LEDs in the length of smart yarn 100 simultaneously, as shown in FIG. 1. In this implementation, the smart yarn can also include a third trace 170 and a fourth trace 180 of similar form on the second side of the flexible substrate 102, and a sensor (e.g., a temperature sensor) can be similarly soldered to trace pads on the third and fourth traces 170, 180 at each component site 114. In particular, the circuit board can define a set of component sites 114 including one LED on the first side of the circuit board and a sensor (or other electrical component) on the second side of the circuit board in each component site 114 such that an LED is arranged over each sensor along the length of the circuit board.

Figure 5A:
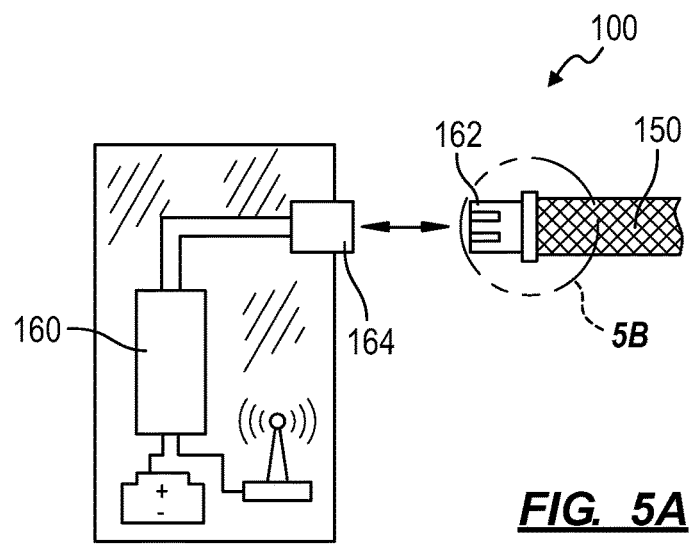
FIGS. 5A and 5B are schematic representations of one variation of the smart yarn.
Figure 5B:
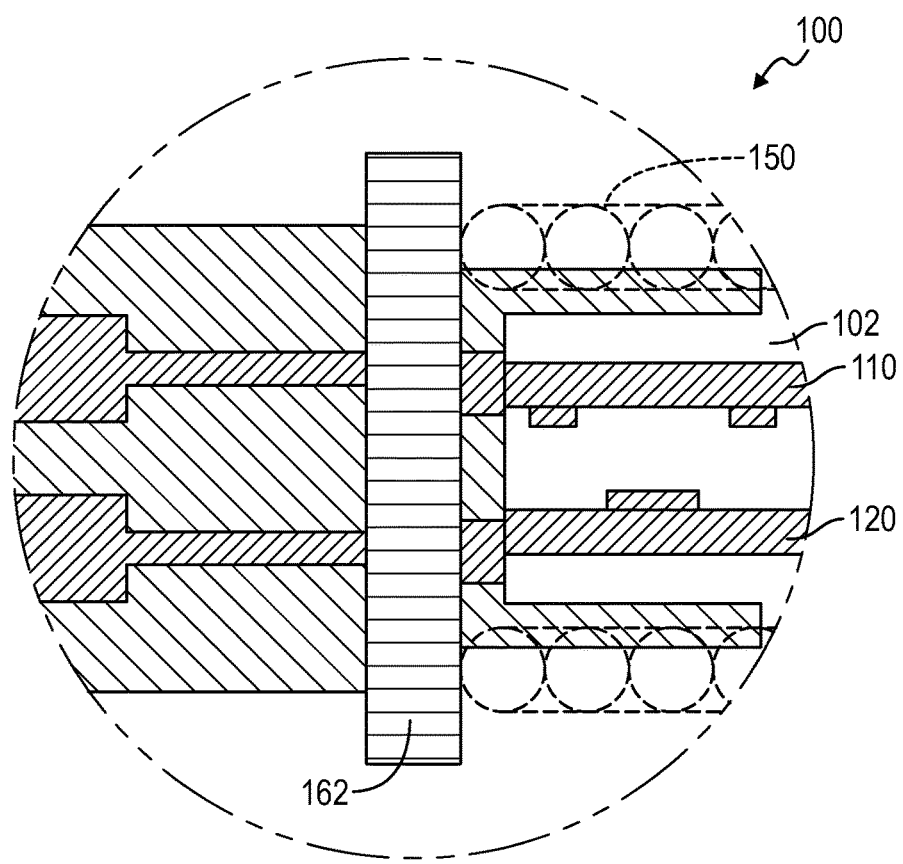

Therefore, the circuit board can include a first trace no and a second trace 120 on a first side of the flexible substrate 102 with a set of LEDs connected in parallel via the two traces on the first side of the flexible substrate 102. All LEDs along the circuit board can thus be simultaneously illuminated by grounding the first trace no and supplying power to the second trace 120 at one end of the circuit board and without cutting the circuit board between LEDs in order to visually indicate the location of each component site 114 along the length of the circuit board, such as once the circuit board is wrapped with the textile sleeve 150 to complete the length of smart yarn 100 as shown in FIG. 1. With the location of each component site 114 along the length of smart yarn 100 thus identified, a section containing one component site 114 can be cut from the length of smart yarn 100. A third trace 170 and a fourth trace 180 on the second side of the flexible substrate 102—connected to a sensor, a signal processor, an integrated communication chip, or any other integrated circuit or electrical component installed at the component site 114 on the second side of the flexible substrate 102—can be exposed by sliding the textile sleeve 150 from the end of the section of circuit board, and this end of the section of circuit board can be connected to a controller 160, as shown in FIGS. 5A and 5B. In this implementation, the controller 160 can then communicate with (e.g., sample) the sensor 130 or other electrical component via the third and fourth traces 170, 180.

In another implementation, the smart yarn includes a pair of parallel traces on one side of the flexible PCB with each trace broken across and defining two offset trace pads at each component site 114, as shown in FIG. 4B. In this implementation, if the completed length of smart yarn 100 is sectioned between adjacent component sites 114, each section of smart yarn can include one component site 114 containing four trace pads with each trace pad connected to one discrete trace segment. In this implementation, a sensor can be installed across (e.g., soldered to) two of the four trace pads at a component site 114, such as across a break in the first trace 110 at the component site 114; and an LED can be installed across the remaining two trace pads at the component site 114, such as across a break in the second trace 120 at the component site 114. Both ends of the section of smart yarn can then be connected to a processor sensor via both sides of the first trace 110 and can selectively illuminate the LED by supplying power to one side of the second trace 120 and ground the second side of the second trace 120.

Alternatively, in the foregoing implementation, the sensor 130 can be installed across a first trace pad at the terminus of a first side of the first trace no and across a second trace pad at the terminus of a first side of the second trace 120 such that the sensor 130 is electrically coupled only to trace sections at the first end of the section of smart yarn. In this implementation, the LED can similarly be installed across a third trace pad at the terminus of a second side of the first trace no and across a fourth trace pad at the terminus of a second side of the second trace 120 such that the LED is electrically coupled only to traces at the second end of the section of smart yarn. The processor can thus sample the sensor 130 via the first end of the section of smart yarn, and a switch can selectively illuminate the LED via the second end of the section of smart yarn.

Yet alternatively, a single integrated circuit or a group of sensors can be installed across all four trace pads at a component site 114 in the section of smart yarn, as shown in FIG. 4D. For example, a three-axis accelerometer and an integrated communication chip can be installed at the component site 114 with: power terminals of the accelerometer and an integrated communication chip connected to a first trace pad at the component site 114; ground terminals of the accelerometer and integrated communication chip connected to a second trace pad at the component site 114; a serial clock input of the integrated communication chip connected to a third trace pad at the component site 114; and power terminals of the accelerometer and integrated communication chip connected to a first trace pad at the component site 114; and a serial output terminal of the integrated communication chip connected to a fourth trace pad at the component site 114. In this example, traces at both ends of the section of smart yarn and the integrated communication chip can be electrically coupled to a processor and to a power supply; and the integrated communication chip can receive a clock signal from the processor via the third trace pad and can serially output digital acceleration values read from each axis of the accelerometer to the processor via the fourth trace pad. In this implementation, an LED can also be installed over the component site 114; and the integrated communication chip can communicate digital acceleration values to and receive digital commands from the processor over the fourth trace pad (e.g., over I2C communication protocol) and switch power to the LED based on digital commands received from the processor. Alternatively, a third trace 170 can be patterned across the back side of the circuit board, an LED can be installed over the third trace 170 on the back side of the circuit board adjacent the component site 114, as shown in FIG. 4A, and power can be supplied to the LED via the third trace 170 to illuminate the LED, thereby indicating the location of the component site 114 containing the LED, the accelerometer, and the integrated communication chip along the section of smart yarn.

However, any number of nested serpentine traces can be fabricated or etched onto one or both sides of the flexible substrate 102. Each trace can: extend through a component site 114, as shown in FIGS. 4A and 4C; or define a break and a pair of trace pads at a component site 114, as shown in FIGS. 4B and 4D, such as to support multiple input and/or output channels at the component site 114.

To visually distinguish two traces formed on one or both sides of the flexible substrate 102, each trace can define a unique repeating pattern or geometry along its length. For example, linear sections of the first serpentine trace can be dentated along (i.e., include rectangular tabs extending outwardly from) one edge, and linear sections of the second serpentine trace—parallel and offset from the first serpentine trace—can be smooth on both sides, as shown in FIG. 4B. In another example, the first and second serpentine traces define inter-digitated tabs (or "dentals"). In this example shown in FIG. 4A, the first serpentine trace includes: linear and end sections 0.1 millimeter in width; and a first sequence of tabs 0.1 millimeter wide by 0.2 millimeter long at a tab pitch distance of 2.0 millimeters extending from the linear and end sections and facing the second serpentine trace. Furthermore, in this example, the second serpentine trace includes: linear and end sections 0.1 millimeter in width; and a second sequence of tabs 0.1 millimeter by wide 0.4 millimeter long at a tab pitch distance of 2.0 millimeters, facing the first serpentine trace, and centered between tabs in the first sequence of tabs in the first trace 110. In this example, once the serpentine circuit is straightened in Block S150 and wrapped in the textile sleeve 150 in Blocks S160 and S162 to form a completed length of smart yarn 100, a human (or machine) can: draw the textile sleeve 150 down from one end of the circuit board to expose the first and second traces 110, 120; and then distinguish the first trace 110 from the second trace 120 by comparing the geometries of the first and second sequences of tabs defined by the first and second traces 110, 120. In this example, with the first and second traces 110, 120 thus identified, the human (or machine) may install the end of the circuit board into a connector 162 or junction block in a correct orientation, as shown in FIGS. 5A and 5B.

The first method S100 can therefore include Block S102, which recites etching a serpentine trace onto a flexible substrate 102, wherein the serpentine trace defines a set of parallel linear sections and a set of end sections coupling adjacent ends of linear sections in the set of parallel linear sections. For example, the flexible substrate 102 can include an aramid-fiber sheet coated on both sides with copper or other electrically-conductive material. In Block S102, a first etch mask (or "resist") defining a serpentine path representative of the first trace 110 can be applied to the first side of the flexible substrate 102, and a second etch mask defining a serpentine path representative of the second trace 120—and which is a mirror image of the first etch mask—can be applied to the second side of the flexible substrate 102 in alignment with the first etch mask. The flexible substrate 102 can then be exposed to etchant to remove conductive material on the first and second sides of the flexible substrate 102 outside of the etch mask. In Block S102, the etch mask can then be removed to expose the first and second traces 110, 120 on the first and second sides of the flexible substrate 102. Alternatively, conductive material can be printed onto one or both sides of the flexible substrate 102 to form the first and second traces 110, 120 in Block S102.

Following formation of the first and second traces 110, 120 on the flexible substrate 102, both sides of the flexible substrate 102 can be coated with an insulative film 104. For example, trace pads at each component site 114 on both sides of the flexible substrate 102 can be masked, a urethane can be sprayed across both sides of the flexible substrate 102, and the mask material can then be removed from the flexible substrate 102 to expose the trace pads prior to installation of one or more electrical components on the flexible substrate 102 in Block S120. Alternatively, the flexible substrate 102 can be coated with the insulative film 104 following installation of electrical components, such as just prior to or just after each component site 114 is potted in Block S130.

However, the flexible substrate 102 and traces can be fabricated in any other way and in any other material(s) in Blocks S102 and S120.

1.6 Electrical Components

The length of smart yarn 100 includes: a sensor coupled to the first set of trace pads 112 at the component site 114; and a light element 140 coupled to the second set of trace pads 122 at the component site 114. Generally, the length of smart yarn 100 includes a sensor (e.g., a thermistor, a pressure sensor, an accelerometer) arranged at a component site 114 and configured to output an electrical signal representative of a biometric signal, environmental signal, or other external signal. The length of smart yarn 100 also includes a light element 140 (e.g., an LED) arranged under a sensor (i.e., on the opposite side of the flexible substrate 102) or next to a sensor (i.e., on the same side of the flexible substrate 102) at each component site 114 and configured to visually indicate the location of each component site 114 (or specifically each sensor) along the length of the circuit board once wrapped with the textile sleeve 150. Block S120 of the first method S100 can therefore include installing an electrical component at a component site 114 on a linear section in the set of parallel linear sections.

In one implementation, two discrete traces—each defining a discrete electrical circuit—are formed on one side of the flexible substrate 102, a sensor is installed on the first trace 110 at each component site 114, and an LED is installed on the second trace 120 at each component site 114 adjacent the sensor 130, such as by an automated SMT pick and place machine, in Block S120. Alternatively, in Block S120: the first trace 110 can be patterned across the first side of the flexible substrate 102; the second trace 120 can be patterned across the second side of the flexible substrate 102; the automated SMT pick and place machine can implement computer vision techniques to register the first side of the flexible substrate 102, can apply solder paste to the first side of the flexible substrate 102 at each component site 114, and can then place a sensor on each component site 114 on the first side of the flexible substrate 102; an operator can flip the flexible substrate 102 on the automated SMT pick and place machine; the automated SMT pick and place machine can implement computer vision techniques to register the second side of the flexible substrate 102, can apply solder paste to the second side of the flexible substrate 102 at each component site 114, can then place an LED on each component site 114 on the second side of the flexible substrate 102; and the flexible substrate 102 can then be passed through a reflow oven to solder the sensors and LEDs to the flexible substrate 102.

Each component on one side of the flexible substrate 102 can be populated with the same type of sensor (e.g., a temperature sensor) or the same combination of electrical components (e.g., a temperature sensor and an LED, an accelerometer and an integrated communication chip). Alternatively, component sites 114 on one side of the flexible substrate 102 can be populated with a variety of electrical components or combinations of electrical components. In this implementation, LEDs can be installed at each component site 114 on the same or opposite side of the flexible substrate 102, wherein each LED is configured to output a color of light uniquely corresponding to the sensor type or combination of electrical components installed at the same component site 114. For example, red LEDs can be paired with temperature sensors, blue LEDs can be paired with moisture sensors, yellow LEDs can be paired with capacitive proximity sensors, and green LEDs can be paired with pressure sensors. In this example, a temperature sensor can be installed at a first component site 114, a moisture sensor can be installed at a second component site 114, a capacitive proximity sensor can be installed at a third component site 114, and a pressure sensor can be installed at a fourth component site 114 along the first trace 110 on the first side of the flexible substrate 102, and this sensor pattern can be repeated along the length of the first trace no. In this example, a red LED can be installed at the first component site 114, a blue LED can be installed at the second component site 114, a yellow LED can be installed at the third component site 114, and a green LED can be installed at the fourth component site 114 along the second trace 120 on the second side of the flexible substrate 102, and this LED pattern can be repeated along the length of the second trace 120. Thus, once (or as) the circuit board is wrapped with the textile sleeve 150 to complete the length of smart yarn 100, the second trace 120 can be connected to a power supply in order to illuminate all of the red, blue, yellow, and green LEDs within the smart yarn, thereby indicating positions of all of the temperature, moisture, proximity, and pressure sensors along the length of smart yarn 100; the length of smart yarn 100 can be cut and each section labeled accordingly. Furthermore, once the length of smart yarn 100 is cut, power can be connected to the second trace 120 in a section of the smart yarn to indicate the type of sensor contained within the section. However, the length of smart yarn 100 can include a light element 140 of any other type configured to output any other color (i.e., wavelength) of light to visually indicate a location of a component site 114 and/or a type of electrical component arranged at the component site 114.

The length of smart yarn 100 is described herein as containing one LED per component site 114, wherein each LED is configured to visually indicate the location and/or type of an adjacent sensor (or other electrical component or combination of electrical components) through the textile sleeve 150. However, the length of smart yarn 100 can additionally or alternatively include any other type of actuator configured to indicate its positions through the textile sleeve 150, such as a mechanical vibrator, a heating element (e.g., a resistance heat), or a speaker (e.g., a buzzer).

1.7 Potting

Block S130 of the first method S100 recites applying sealant 106 between the electrical component and the flexible substrate 102. Generally, in Block S130, a potting material can be applied to a component site 114 on one or both sides of the flexible substrate 102 in order to seal the sensor 130 and LED (and/or other electrical components) to the flexible substrate 102. For example, on the flexible substrate 102, sensors and LEDs are passed through a reflow oven in Block S120, the flexible substrate 102 can be returned to the automated SMT pick and place machine, which can automatically dispense a volume of epoxy resin at each component site 114 on the first and second sides of the flexible substrate 102. Alternatively, an insulative film 104 can be sprayed on both sides of the flexible substrate 102, including over traces and electrical components in order to seal the traces and electrical components to the flexible substrate 102. However, a sealant 106 or other potting material can be applied to component sites 114 on the flexible substrate 102 in any other suitable way in Block S130

1.8 Trimming

Block S140 of the first method S100 recites removing regions of the flexible substrate 102 beyond the serpentine trace to form a flexible serpentine circuit board. Generally, in Block S140, the automated SMT pick and place machine or other apparatus can pierce the flexible circuit board around the serpentine trace(s) in order to free the serpentine circuit board from the rectangular flexible substrate 102.

In one implementation described above in which the length of smart yarn 100 includes one trace on a side of the circuit board, the automated SMT pick and place machine or other apparatus can cut a line parallel to (and offset from, such as by 0.1 millimeter) the edge of both sides of the trace to free the serpentine circuit board from the flexible substrate 102. Similarly, in the implementation described above in which the length of smart yarn 100 includes two traces on one side of the circuit board, the automated SMT pick and place machine or other apparatus can cut a line parallel to (and offset from) the outer edges of the two traces to free the serpentine circuit board from the flexible substrate 102. For example, the automated SMT pick and place machine or other apparatus can cut the flexible substrate 102 with a laser, with a rolling knife edge, with a water jet, or with any other suitable cutting tool in Block 140.

The automated SMT pick and place machine or other apparatus can also cut an interrupted line along both sides of the trace(s) on one side of the flexible substrate 102 in order to maintain location of the serpentine circuit board while the full length of the serpentine circuit board is cut from the flexible substrate 102. For example, the automated SMT pick and place machine can perforate the flexible substrate 102 along both sides of the serpentine circuit board to form tabs between the serpentine circuit board and the remaining flexible substrate 102, and the serpentine circuit board can be pulled from the flexible substrate 102 to tear the tabs, thereby freeing the serpentine circuit board from the remaining flexible substrate 102.

However, the serpentine circuit board can be cut from the flexible substrate 102 in any other way in Block S140. The serpentine circuit board can also be cut from the flexible substrate 102 prior to installation of the sensors and LEDs or prior to application of sealant 106 around the sensors and LEDs.

1.9 Packing and Wrapping Fibers

The length of smart yarn 100 includes a textile sleeve 150, which includes: packing fibers 152 arranged axially along the flexible substrate 102 and over the sensor 130 and the light element 140; and wrapping fibers 154 wrapped radially over the packing fibers 152 along the flexible substrate 102. Generally, the serpentine circuit board can be straightened, and packing fibers 152 can be arranged along the length of the straightened circuit board and can function to buffer the circuit board from impact. The packing fibers 152 can also exhibit greater tensile strength than the circuit board and can resist strain across the straightened circuit board when a section of smart yarn is tensioned in order to protect the circuit board—within the section of smart yarn—from tearing under such tension. Furthermore, the wrapping fibers 154 can be wrapped, woven, or braided around the packing fibers 152 and the circuit board to further buffer the circuit board from impact and to constrain the packing fibers 152 in position around and substantially axially parallel to the circuit board. The packing and wrapping fibers 154 can therefore cooperate to protect the circuit board from both exposure (e.g., to moisture or dirt) and mechanical stress, such as when woven into a garment and when the garment is worn.

The first method S100 can therefore include: deforming a first end section in the set of end sections interposed between a first linear section and a second linear section in the set of parallel linear sections to substantially axially align the first linear section and the second linear section in Block S150; arranging packing fibers 152 axially along the first linear section, the first end section, and the second end section in Block S160; and wrapping the packing fibers 152 with wrapping fibers 154 to form a length of smart yarn in Block S162. Generally, the serpentine circuit board can be straightened following (or during) removal from the flexible substrate 102 in Block S150, strengthened axially with packing fibers 152 arranged along the length of the straightened circuit board in Block S160, and wrapping fibers 154 can be wrapped around the packing fibers 152 and the straightened circuit board in Block S162 in order to constrain the packing fibers 152 around the straightened circuit board. The length of smart yarn 100 can therefore include multiple sensors that are assembled onto a single flexible substrate 102 in one process per side of the flexible substrate 102. The flexible substrate 102 is then cut around the serpentine trace(s) to release the serpentine circuit board—containing electrical components mounted on the trace(s)—from the flexible substrate 102, and the serpentine circuit board is straightened and wrapped with packing and wrapping fibers 154 to complete the length of smart yarn 100, thereby necessitating no soldering or installation of thin wire interconnects between electrical components along the length of smart yarn 100.

In one implementation, once the flexible substrate 102 is perforated around the trace(s), as described above, one end of the circuit board is passed through an eyelet and is connected to a carrier (or "spool"). The carrier is then rotated to tension the serpentine circuit board and to load the serpentine circuit board onto the carrier as the circuit board is torn from the flexible substrate 102 in Block S140. In particular, as the serpentine circuit board is tensioned between the carrier and the flexible substrate 102, curvilinear sections of the circuit board can deform into substantially axial alignment with linear sections of the circuit board entering the carrier. Once the circuit board is fully removed from the flexible substrate 102 and loaded onto the carrier, the carrier can be loaded into a core carrier position within a yarn-processing machine. Carriers containing polyester, polyamide, cotton, nylon, or packing and wrapping fibers 154 of any other type can be similarly loaded into pacing and wrapping carrier positions within the yarn-processing machine, as shown in FIG. 1. A free end of the circuit board can then be passed through an eye of the yarn-processing machine and the yarn-processing machine started. The yarn-processing machine can then substantially simultaneously: unwind packing fibers 152 from corresponding carriers; orient these packing fibers 152 along the length of the circuit board (i.e., in a warp configuration) in Block S160; unwind wrapping fibers 154 from corresponding wrapping carriers; and wrap (or "braid," "weave") wrapping fibers 154 around the packing fibers 152 and the circuit board (i.e., in a weft configuration) in Block S162 as the circuit board is drawn through the eye of the yarn-processing machine, as shown in FIG. 1. The circuit board, packing fibers 152, and wrapping fibers 154 can thus exit the yarn-processing machine as completed smart yarn. Furthermore, end sections of the circuit board can deform and straighten as the circuit board is tensioned such that the circuit board can pass freely through the eye of the yarn-processing machine and such that end sections of the circuit board remain constrained in substantially straight orientations by the packing and wrapping fibers 154 once the length of smart yarn 100 is completed.

In a similar implementation, the serpentine circuit board can be separated from the flexible substrate 102, straightened, and wrapped directly with packing and wrapping fibers 154 by a yarn-processing machine in Blocks S140, S150, S160, and S162. However, the circuit board can be separated from the flexible substrate 102 and wrapped in any other suitable way in Blocks S140, S150, S160, and S162.

1.10 Sensor Location Detection

As shown in FIG. 1, one variation of the first method S100 includes Block S164, which recites identifying a location of a sensor along the length of smart yarn 100 based on light output by an adjacent light element 140. Generally, each sensor arranged on the circuit board can be paired with an LED arranged on a separate trace (i.e., on a separate circuit) along the length of the circuit board, as described above. Once the circuit board is wrapped with packing and wrapping fibers 154 in Blocks S160 and S162, the sensor 130 may be obscured and its location no longer easily detectible visually or tactilely. The circuit board can thereby be connected to a power supply to supply power to LEDs along the length of the smart yarn; with the LEDs thus illuminated, positions of adjacent sensors can be physically marked directly on the length of smart yarn 100, such as with chalk, ink, or paint. Alternatively, the smart yarn can be kinked on one or both sides of an illuminated LED to physically indicate the position of the LED and its paired sensor once the LED is deactivated. Yet alternatively, a human operator or a computer system can generate a lookup table or a virtual model representative of the length of smart yarn 100 and noting distances between the LED/sensor pairs and a reference point on the length of smart yarn 100.

In one implementation shown in FIG. 1, the yarn-processing machine includes an optical detector and an ink applicator (e.g., an ink pen) mounted to an actuator adjacent and facing the eye of the yarn-processing machine. In this implementation, the circuit board can include a set of LEDs connected in series to a pair of traces on the second side of the circuit board, including one LED arranged under each sensor (or other electrical component) arranged along the top of the circuit board. The leading end of the circuit board—once fed into the eye of the yarn-processing machine—can be connected to a power supply to illuminate each LED. When the yarn-processing machine is then actuated, the optical detector (e.g., a photo detector) facing the completed smart yarn passing through the eye can detect a section of illuminated smart yarn and can trigger the actuator to advance the ink applicator to mark the illuminated region of smart yarn with ink (or with paint or chalk, etc.), as shown in FIG. 1.

In the foregoing implementation, the ink applicator can apply a colored ink, such as black or green ink, to the smart yarn. Alternatively, the ink applicator can apply a fluorescent ink that is substantially invisible to the human visible spectrum except under ultraviolet light. The length of smart yarn 100 can then be processed under ultraviolet (or "black") light, such as to form a garment in Block S170, such that ink applied over each LED/sensor pair in a final product containing the smart yarn is substantially invisible to humans.

Furthermore, in the foregoing implementation, the automated braiding system can include multiple ink applicators containing different ink colors; and the optical detector can detect various wavelengths of light, such as red, green, yellow, and blue light. The optical detector can thus trigger advancement of select ink applicators based on the ink color in the ink applicators and the color of light output by each LED along the length of the smart yarn, such as for the length of smart yarn 100 containing different sensors and LEDs configured to output corresponding colors of light at various component sites 114 along its length, as described above.

Alternatively, once wrapped in the textile sleeve 150 in Blocks S160 and S162, the length of smart yarn 100 can be laid out manually by a human operator, one end of the circuit board can be connected to a power supply to illuminate LEDs contained within the textile sleeve 150, and the human operator can manually mark the position of each illuminated LED—and therefore its corresponding sensor—along the length of smart yarn 100.

However, the position of each LED and its corresponding sensor can be detected and noted in any other way in Block S164.

1.11 Sectioning

Once the length of smart yarn 100 is completed in Blocks S160 and S162 and once the location of each LED is detected in Block S164, the length of smart yarn 100 can be cut into discrete sections containing one (or more) sensors. For example, the length of smart yarn 100 can be cut between adjacent sensors to create multiple discrete sections of smart yarn—each containing one sensor—from a single flexible substrate 102 processed into one length of smart yarn 100 between Blocks S102 and S162. In a similar example, once the location of each LED/sensor pair is identified in Block S164, a section corresponding to an end section of the circuit board can be removed between each adjacent LED/sensor pair along the length of smart yarn 100, thereby yielding a set of smart yarn sections, each containing one sensor and only linear sections of the serpentine circuit board removed from the flexible substrate 102 in Block S140.

Alternatively, in the implementation described above in which a yarn-processing machine winds packing and wrapping fibers 154 around the circuit board, the second end of the circuit board—opposite the first end of the circuit board first loaded into the eye of the yarn-processing machine—can be connected to the power supply to illuminate LEDs along the length of the circuit board, and the yarn-processing machine can include a cutting module across its eye. A controller 160 controlling the yarn-processing machine can then trigger the cutting module to cut a completed section of smart yarn from the yarn-processing machine once a target length of smart yarn has passed through the eye of the yarn-processing machine following detection of an illuminated LED within the section of smart yarn. However, the length of smart yarn 100 can be sectioned in any other way.

1.12 Weaving into Garment

Block S170 of the first method S100 recites weaving a section of the length of smart yarn 100 into a garment. Generally, in Block S170, one or more sections of smart yarn—cut from the length of smart yarn 100—can be knit into a garment.

In one example, six discrete sections of smart yarn, each containing one temperature sensor, can be interwoven with cotton or polyester yarn to form a sock including two temperature sensors arranged across the phalange region, two temperature sensors arranged across the metatarsal, and two temperature sensors arranged across the tarsal region of the bottom of the sock. In this example, one end of each section of smart yarn can terminate near an ankle region of the sock; a connector 162 can be installed on this end of each section of smart yarn, as shown in FIGS. 5A and 5B; each connector 162 can be installed in a receptacle 164 on a control board arranged on the ankle region of the sock; and a controller 160 integrated into the control board can sample the temperature sensors while the sock is worn by a user in order to track temperatures of the phalange, metatarsal, and tarsal regions of the user's foot.

Outside of a component region, a section of smart yarn can include a substantially uniform cross-section of traces. The section of smart yarn can therefore be trimmed to length once woven into a garment (e.g., near a control board), and the textile sleeve 150 can be drawn down from the end of the section of smart yarn to expose traces on both sides of the section of circuit board contained within the section of smart yarn. A polymer (e.g., nylon) connector 162 can then be snapped over the end of the section of smart yarn, and the connector 162 can be installed in a receptacle 164 on a control board to electrically couple the section of smart yarn to a controller 160. The connector 162 can: be crimped onto the end of the circuit board section; can be retained on the end of the circuit board section via a barb that pierces the circuit board; can include a ratchet that constrains the end of the circuit board section within a receiver; can be glued or potted onto the end of the circuit board section; or can be installed on and constrain the end of the circuit board section in any other way. However, the connector 162 can be installed on the end of the circuit board section without soldering in order to simplify connection between the section of smart yarn and the controller 160 or other junction block.

Alternatively, the entire length of smart yarn 100 can be woven into a complete garment or a complete section of a garment. For example, component sites 114 can be fabricated on particular locations on the flexible substrate 102 and populated with sensors and actuators (e.g., LEDs) such that the completed length of smart yarn 100 constructed from the flexible substrate 102 can be woven into one garment or one garment section with sensors arranged at target locations on the garment or garment section. Similarly, sections of the smart yarn containing multiple component sites 114—and therefore multiple sensors—can be woven into a garment. However, all or a section of the length of smart yarn 100 can be incorporated into a garment in any other way.

2. Second Method: Discrete Serial Sensing Elements

Figure 12:
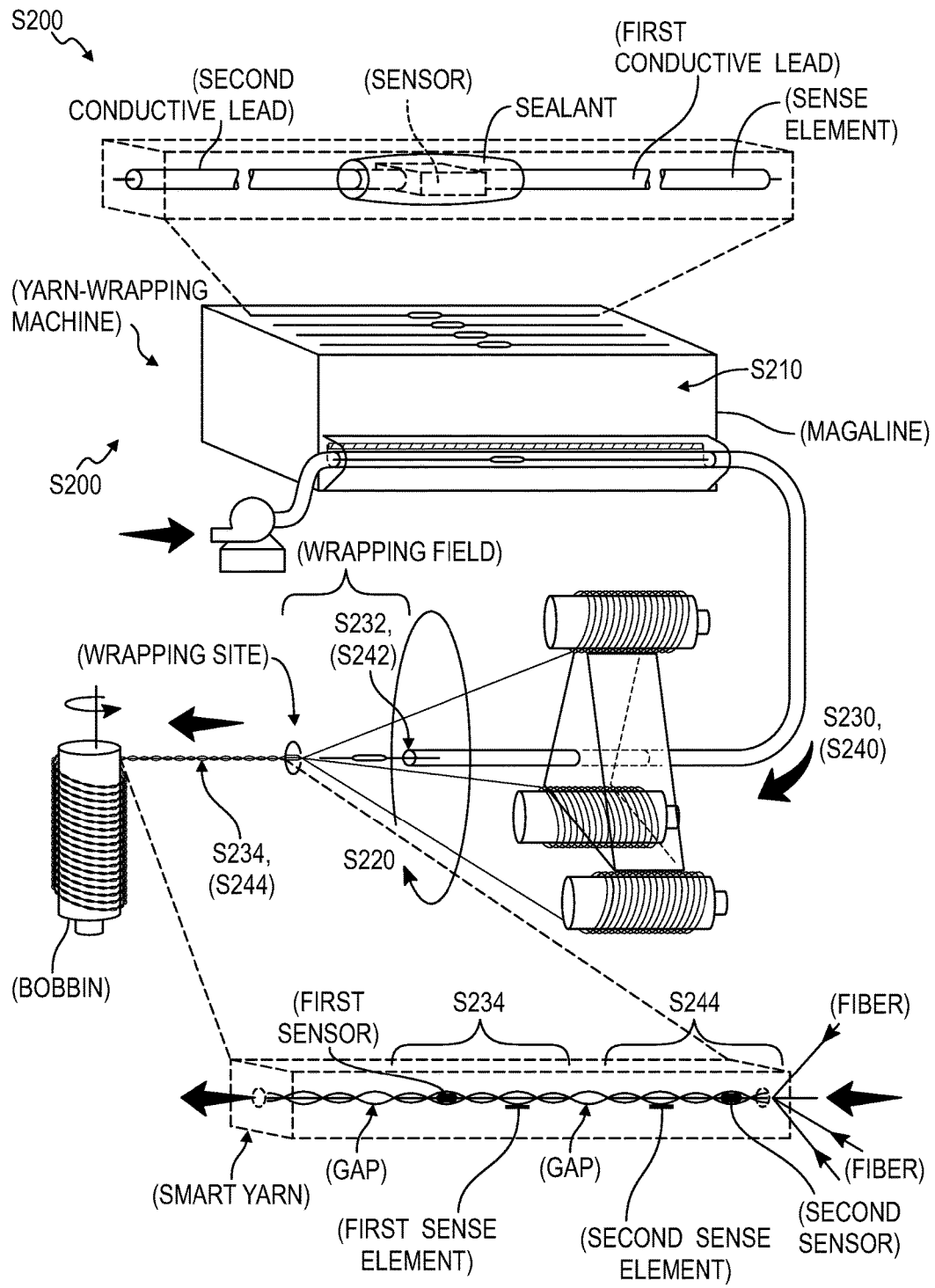
FIG. 12 is a flowchart representation of a second method.
Figure 13:
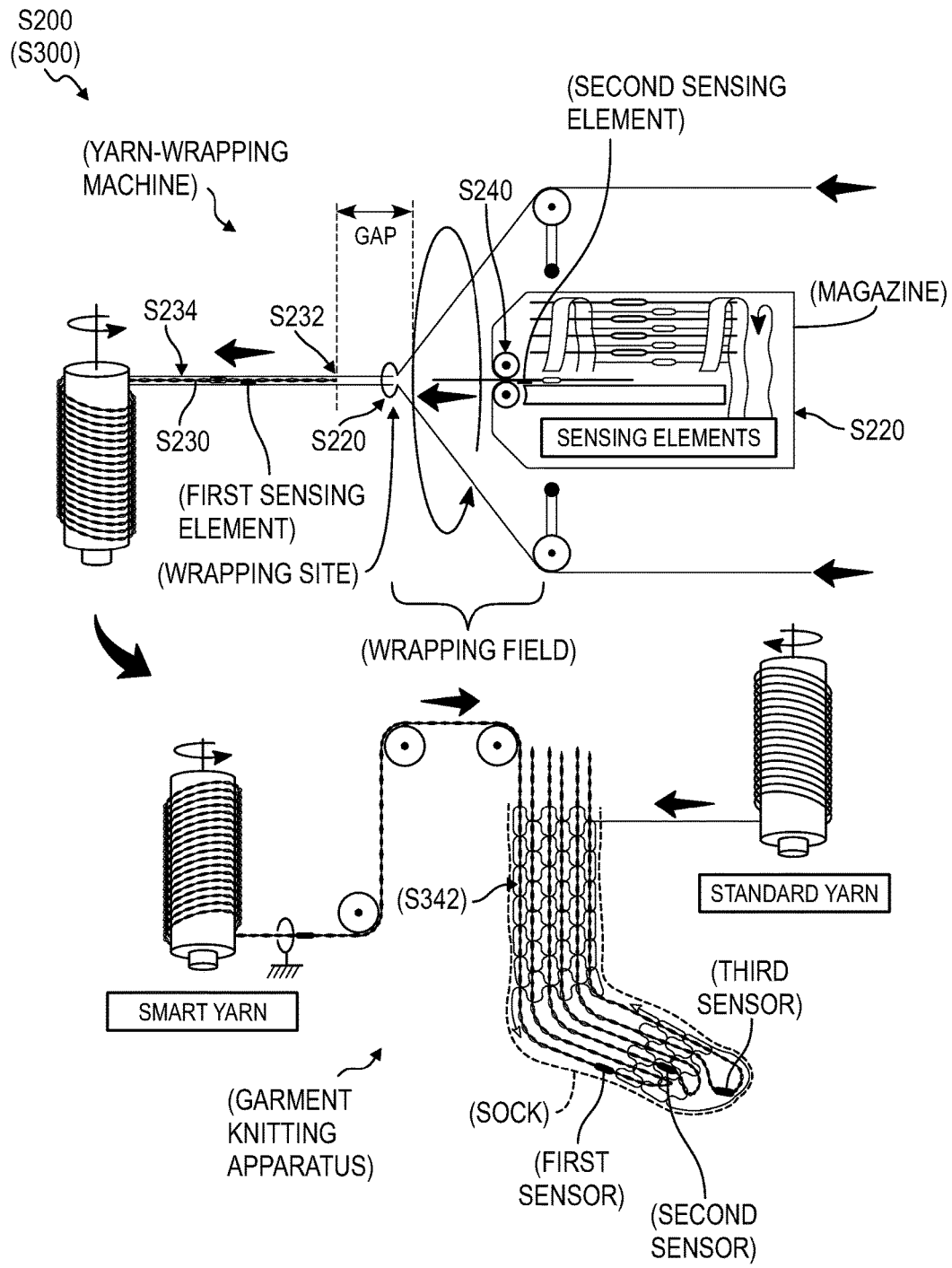
FIG. 13 is a flowchart representation of one variation of the second method.

As shown in FIGS. 12 and 13, a second method S200 for producing a smart yarn includes: aligning a set of sensing elements offset along a lateral axis in a magazine in Block S210, wherein each sensing element in the set of sensing elements includes a sensor module, a first conductive lead extending from a first side of the sensor module along a longitudinal axis perpendicular to the lateral axis, and a second conductive lead extending from a second side of the sensor module opposite the first side and along the longitudinal axis; wrapping a set of fibers into a yarn within a wrapping field in Block S220; feeding a leading end of a first sensing element, in the set of sensing elements, from the magazine into the wrapping field in Block S230; releasing the first sensing element from the magazine into the wrapping field in Block S232; encasing the first sensing element between the set of fibers within the yarn in Block S234; in response to a trailing end of the first sensing element passing through the wrapping field following release of the first sensing element from the magazine into the wrapping field, feeding a leading end of a second sensing element, in the set of sensing elements, from the magazine into the wrapping field in Block S240; releasing the second sensing element from the magazine into the wrapping field in Block S242; and encasing the second sensing element between the set of fibers and longitudinally offset behind the first sensing element within the yarn in Block S244.

One variation of the second method S200 shown in FIGS. 12 and 13 includes: storing, in a dispenser, a set of sensing elements offset along a lateral axis in Block S210, wherein each sensing element in the set of sensing elements includes a sensor module, a first conductive lead extending from a first side of the sensor module along a longitudinal axis perpendicular to the lateral axis, and a second conductive lead extending from a second side of the sensor module opposite the first side and along the longitudinal axis; feeding a leading end of a first sensing element in Block S230, in the set of sensing elements, from the dispenser toward a wrapping site; at the wrapping site, wrapping a set of fibers around the first sensing element to form a yarn in Block S234; in response to a trailing end of the first sensing element passing the wrapping site, feeding a leading end of a second sensing element, in the set of sensing elements, from the dispenser toward the wrapping site in Block S240; and, at the wrapping site, wrapping the set of fibers around the second sensing element to continue the yarn in Block S244, the leading end of the second sensing element longitudinally offset behind the trailing end of the first sensing element within the yarn.

2.1 Applications

Generally, Blocks of the second method S200 can be executed by a yarn (or thread, fiber, or similar) processing machine to produce a length of smart yarn. In particular, the yarn-processing machine can: receive or store a dispenser (e.g., a magazine) containing a set of sensing elements—each containing a sensor (e.g., a temperature sensor) connected to conductive leads on each end—arranged in parallel; inject discrete, linear sensing elements from the dispenser into a wrapping field in series; and sequentially wrap multiple discrete fibers (e.g., spun natural fibers and/or continuous synthetic filaments) around these sensing elements to yield a continuous length of smart yarn containing sensing elements—and specifically sensors—arranged in series.

By handling sensing elements stored in parallel, the yarn-processing machine can leverage existing electronics manufacturing and supply chain infrastructure for production of short, discrete (i.e., non-continuous) sensing elements. For example, the yarn-processing machine can receive a magazine containing sensing elements in the form of: a discrete sensor with one elongated wire extending from each of two opposite ends; an elongated PCB with a sensor placed between two linear and parallel traces; or a serpentine or boustrophedonic trace with a set of sensors placed along linear sections of the trace, as described above. However, existing yarn, garment, and textile manufacturing and supply chain infrastructure for production of textiles may be adapted for continuous or very-long yarn lengths, which may conflict with capabilities of existing electronics manufacturing and related electronics supply chains. Therefore, the yarn-processing machine can execute Blocks of the second method S200 to marry short, discrete (i.e., non-continuous) sensing elements produced with existing electronics manufacturing to existing textile manufacturing processes by serially injecting sensing elements—stored in parallel—into a wrapping field in which discrete fibers are spun or twisted into multi-filament yarn, thereby yielding a continuous or very-long length of smart yarn containing many sensors arranged in series, each connected to its own conductive leads.

Smart yarn thus produced according to the second method S200 can then be combined with standard yarn (i.e., excluding sensing elements) to knit or otherwise fabricate a smart garment, such as a temperature-sensing-enabled sock, as described above. For example, as an automated knitting machine knits a sock from standard yarn, the automated knitting machine can: knit a leading end of a segment of the smart yarn—containing a sensing element and leading a sensor—from a bobbin into an opening of the sock; knit the length of the segment of smart yarn along the sole of the sock with the sensor located near a target location on the sole of the sock; and knit the segment of smart yarn succeeding the sensor back toward the opening of the sock; cut the segment from the length of smart yarn proximal the opening of the sock; trim the smart yarn on the bobbin back to a conductive lead of a next sensing element; and repeat the foregoing process to knit the next sensing element and additional sensing elements along the length of smart yarn into the sock with their corresponding sensors arranged near corresponding target locations across the sole of the sock.

As described above, the smart yarn produced by the yarn-processing machine according to the second method S200 is described below as including a series of temperature sensors and manufactured for incorporation into a sock. However, all or a section of the length of smart yarn 100 be similarly incorporated into any other textiles and can include any other type of sensor.

2.2 Sensing Elements and Storage

Block S210 of the second method S200 recites aligning a set of sensing elements offset along a lateral axis in a magazine in Block S210, wherein each sensing element in the set of sensing elements includes a sensor module, a first conductive lead extending from a first side of the sensor module along a longitudinal axis perpendicular to the lateral axis, and a second conductive lead extending from a second side of the sensor module opposite the first side and along the longitudinal axis. Generally, in Block S210, the yarn-processing machine receives a set (e.g., hundreds, thousands) of short, discrete sensing elements and stores these sensing elements in a parallel arrangement—that is, with sensors in the set of sensing elements substantially aligned along a lateral axis or lateral plane, and with linear conductive leads extending from each of these sensors along longitudinal axes perpendicular to the lateral axis or lateral plane. By storing these sensing elements in a parallel arrangement, such as in a magazine or cartridge, the yarn-processing machine can achieve a relatively short sensing element magazine length while serially inserting sensing elements into a relatively long lengths of smart yarn.

2.2.1 Fabricated Wire

In one implementation shown in FIG. 12, the yarn-processing machine handles discrete, linear sensing elements fabricated from sensors and insulated conductive wire.

For example, existing electronics manufacturing techniques can be implemented: to solder a first insulated wire (e.g., of a first color) onto a first side of a sensor (e.g., a voltage supply side of a thermistor or other temperature sensor); and to solder a second insulated wire (e.g., of a second color) onto a second side of the sensor (e.g., a sensor output side of the thermistor or other temperature sensor). In this example, the sensor can define a relatively small package size, such as a surface-mount integrated sensor, in order to accommodate a narrow yarn size, and the first and second insulated wires can be soldered or otherwise directly connected to corresponding sides of the sensor to define the first and second conductive leads. These insulated wires can be cut long (e.g., 200 millimeters each) and drawn (or left) straight such that these insulated wires extend in parallel and opposite directions from the sensor. The sensor and adjacent ends of the insulated wires can then be coated (e.g., encased) in a non-conductive potting material, such as a polyester or epoxy, in order to seal open input and output sides of the sensor and to support junctions between the sensor and the insulated wires from bending, breaking, and other damage.

Figure 10:
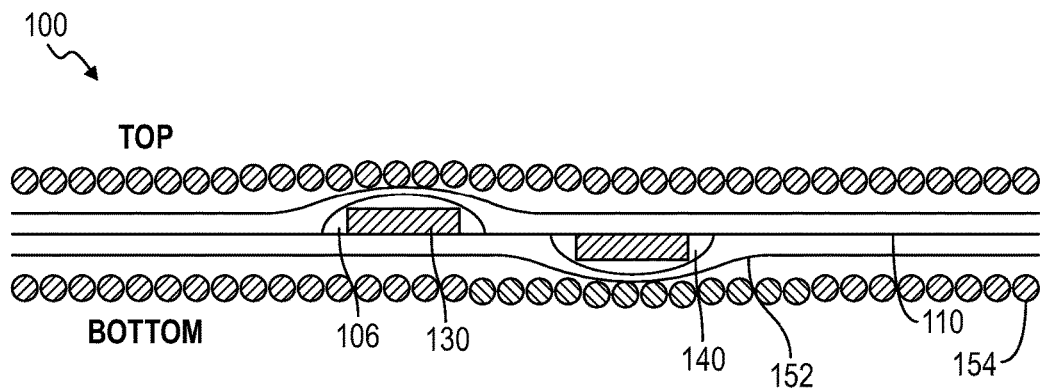
FIG. 10 is a schematic representation of one variation of the smart yarn.

In one variation, the sensor and conductive leads can be bundled with a second electrical component connected to a second set of conductive leads, such as a second sensor (e.g., a second thermistor for redundancy, a pressure sensor, an ambient light sensor, etc.) or an actuator (e.g., a light element, a piezoelectric transducer). For example, in this variation, existing electronics manufacturing techniques can be implemented: to solder a third insulated wire (e.g., of a third color) onto a first side of a second electrical component (e.g., a voltage supply side of an LED or other light element); to soldering a fourth insulated wire (e.g., of a fourth color) onto a second side of the second electrical component (e.g., a ground side of the LED or other light element); and to apply non-conductive potting material around the second electrical component and adjacent ends of the third and fourth insulated wires, as described above. The first insulated wire and the third insulated wire can then be twisted along the longitudinal axis of the sensing element to form the first conductive lead and the second insulated wire and the fourth insulated wire can be twisted along the longitudinal axis of the sensing element to form the second conductive lead with the sensor adjacent the second electrical component (and slightly offset from the second electrical component along the longitudinal axis, as shown in FIG. 10). Non-conductive potting material can additionally or alternatively be applied around the sensor, the second electrical component, and the insulated wires once these elements are thus assembled into one sensing element.

In this variation, once a segment of smart yarn containing this sensing element is knitted or otherwise integrated into a garment: yarn spun, twisted, or woven around these sensing elements can be peeled back from the sensing element near a control module integrated into or connected to the garment; and insulated wires connected to the sensor and to the second electrical component can be distinguished by color and then connected to corresponding junctions of the control module, thereby enabling a controller within the control module to read sensor data (e.g., temperature values) from the sensor and to control outputs of the second electrical component (e.g., to activate the LED). However, in this variation, the sensor, the second electrical component, this set of insulated wires (and additional electrical components and insulated wires) can be assembled in any other way to form one sensing element.

Multiple units of this sensing element can be fabricated and stored in parallel in preparation for insertion into a multifilament yarn. In one example shown in FIG. 13: a set of sensing elements are arranged in parallel (i.e., with their sensors aligned and offset along a lateral axis perpendicular to their longitudinal axes); a first strip of adhesive tape is applied across the set of sensing elements along leading ends of these sensing elements; and a second strip of adhesive tape is applied across the set of sensing elements along trailing ends of these sensing elements opposite their leading ends. To insert a next sensing element into the wrapping field described below, the yarn-processing machine can separate or tear a next-available sensing element from these strips of tape (e.g., by drawing the sensing element forward through a set of rollers, as shown in FIG. 13) and then feed this sensing element forward into the wrapping field.

In another example, sensing elements are arranged in parallel on cardstock with ends of these sensing elements fed into and retained by bores or slits in the cardstock. To insert a next sensing element into wrapping field described below, the yarn-processing machine can tear the card stock around the next-available sensing element or draw this sensing element through the cardstock from these strips of tape (e.g., by drawing the sensing element forward through a set of rollers) and then feed this sensing element forward into the wrapping field.

In yet another example shown in FIG. 12, a set of sensing elements are stored loose in a magazine, such as a plastic or metal container. In this example, the magazine can include: a holding area configured to house loose sensing elements; a funnel extending down from the holding area; a linear receiver arranged below the funnel, extending along the funnel, and terminating at an outlet; and a bolt configured to run inside the receiver toward the outlet. During operation: the holding area can be loaded with sensing elements arranged with their longitudinal axes substantially parallel to the receiver; the funnel can feed sensing elements down toward the receiver; the receiver can accept one sensing element when the bolt is retracted; the bolt can be driven forward toward the outlet (e.g., at a rate corresponding to a yarn output rate from the wrapping field) to dispense this sensing element into the wrapping field; and the bolt can then be retracted to release a next sensing element into the receiver before repeating this process. In this example, the magazine can also include a set of digitated wheels arranged between the holding volume and the receiver and configured—when rotated—to collect individual sensing elements from the funnel and to load individual sensing elements into the receiver.

In a similar example, the set of sensing elements are stored loose in a magazine with a holding area, funnel, receiver, and/or digitated wheels, as described above. In this example, the magazine can include a set of rollers arranged along the receiver parallel and configured to contact a sensing element in the receiver and to drive the sensing element forward into the wrapping field when rotated in a forward direction.

However, in this implementation, the sensing elements can be stored in any other way and fed from a magazine or other dispenser in any other way.

Therefore, the yarn-processing machine can sequentially inject discrete, wire-based sensing elements (e.g., stored in parallel in order to limit processing space and to accommodate existing electronics manufacturing techniques) into the wrapping field over time to produce a length of smart yarn containing a relatively large number of sensing elements arranged in series. However, the yarn-processing machine can be loaded with wire-based sensing elements of any other type or format in Block S210.

2.2.2 PCB Strips

In another variation shown in FIGS. 6 and 11, a set of sensing elements are fabricated on a flexible PCB that is then diced to separate these sensing elements before these discrete sensing elements are fed into the wrapping field during production of a length of smart yarn. For example, existing electronics manufacturing techniques can be implemented to etch a set of traces onto a flexible substrate (e.g., a flexible PCB), wherein these traces are linear, parallel, and offset laterally (i.e., along a common lateral axis), and wherein each trace includes a break that defines a component site. In this example, electrical components can be installed at component sites defined by each trace, such as by depositing solder paste on each side of each component site, placing an electrical component in solder paste at each component site, and passing the flexible substrate through a reflow oven to fix these electrical components in place at the component site and electrically coupled to each side of their corresponding trace. The flexible substrate, traces, and electrical components can then be coated with an insulative material, such as a polyester or epoxy coating.

The flexible substrate can then be diced parallel to and between these traces to form a set of discrete sensing elements. In one implementation, the flexible substrate is diced outside of the yarn-processing machine, such as with a laser, a blade drawn along the length of the flexible substrate, or with a shear die spanning the length of the flexible substrate. These sensing elements can then be stacked or loosely loaded into a magazine, such as described above. Later, the magazine can be loaded into the yarn-processing machine, and a set of digitated wheels, rollers, and/or other actuators within the magazine or within the yarn-processing machine can cooperate to serially dispense individual sensing elements from the magazine into the wrapping field.

Alternatively, the flexible substrate—uncut and with multiple sensing elements intact—can be loaded into the yarn-processing machine. The yarn-processing machine can then serially dice sensing elements from the flexible subtract, such as: by passing a laser linearly along the length of the flexible substrate between a next sensing element and a subsequent sensing element; by drawing a fixed or rotary blade along the length of the flexible substrate between the next sensing element and the subsequent sensing element; or by indexing the flexible substrate forward to center an interstice between the next sensing element and the subsequent sensing element under a shear die and then advancing the shear die into the flexible substrate; etc. With a next sensing element thus separated from the flexible substrate, the yarn-processing machine can implement methods and techniques to drive this sensing element forward and into the wrapping field. In this implementation, the yarn-processing machine can thus store sensing elements—arranged in parallel—in an uncut sheet and can then selectively cut sensing elements from these sheets before inserting these sensing elements into the wrapping field. In this implementation, the yarn-processing machine can also receive a stack of such sheets of uncut sensing elements and can sequentially process these sheets in real-time in preparation for dispensing sensing elements into the wrapping field for production of smart yarn.

Therefore, the yarn-processing machine can sequentially inject discrete, PCB-based sensing elements (e.g., stored in parallel in order to limit processing space and to accommodate existing electronics manufacturing techniques) into the wrapping field over time to produce a length of smart yarn containing a relatively large number of sensing elements arranged in series. However, in this variation, sensing elements can be defined or fabricated in any other way on a common flexible substrate and can be separated from the flexible substrate in any other way and at any other time prior to being fed into the wrapping field to produce a length of smart yarn. Furthermore, the yarn-processing machine can be loaded with PCB-based sensing elements of any other type or format in Block S210.

2.2.3 Serpentine PCB

In another variation shown in FIG. 1, the yarn-processing machine: is loaded with a continuous serpentine (or boustrophedonic) sensing element containing multiple sensors arranged along parallel and offset traces, such as described above; elongates this sensing element; and feeds this sensing element into the wrapping field to produce a length of smart yarn connecting multiple sensing elements arranged in series. For example and as described above, existing electronics manufacturing techniques can be implemented to etch a serpentine trace onto a flexible substrate, including: a first set of linear sections extending parallel to the longitudinal axis, offset along the lateral axis, and defining conductive leads; a first set of curvilinear sections coupling adjacent ends of linear sections in the first set of linear sections; and a component site coincident each linear section in the first set of linear sections. In this example, an electrical component (e.g., a sensor) can be installed on a trace and sealant can be applied over the electrical component and the flexible substrate at each component site on the flexible substrate.

In the foregoing example, the serpentine trace can then be separated from regions of the flexible substrate beyond the serpentine trace to form a continuous flexible serpentine circuit board defining a set of linear traces extending parallel to a longitudinal axis and containing a set of sensing elements offset along a lateral axis perpendicular to the longitudinal axis. This flexible serpentine circuit board can then be loaded into the yarn-processing machine, such as into a magazine or other dispenser, and the yarn-processing machine can feed a start end of the first flexible serpentine circuit board from its dispenser directly into the wrapping field, such as by actuating a set of rollers in the dispenser to drive the start end of the flexible serpentine circuit board forward and into the wrapping field, as described above. Once the start end of the flexible serpentine circuit board is wrapped with fibers at the wrapping site, the yarn-processing machine can release tension on the flexible serpentine circuit board to permit yarn exiting the wrapping field to draw the remainder of the flexible serpentine circuit board out of its dispenser and into the wrapping field. Therefore, as the flexible serpentine circuit board is fed from the magazine into the wrapping field, the yarn-processing machine can sequentially deform curvilinear sections—in the first set of curvilinear sections—in the flexible serpentine circuit board in order to axially align these curvilinear sections of the flexible serpentine circuit board to their adjacent linear sections, thereby transitioning sensors in the flexible serpentine circuit board from a parallel arrangement around the flexible substrate to a serial arrangement in the smart yarn.

Alternatively, the rather than fully separating the serpentine trace from regions of the flexible substrate beyond the flexible substrate, the flexible substrate can be perforated between the serpentine trace and these regions of the flexible substrate beyond the serpentine trace, such as with a die cutter or laser, as described above. The perforated substrate can then be loaded into the yarn-processing machine, and the yarn-processing machine can tear the start end of the flexible serpentine circuit board from the perforated substrate (or engage the start end of the flexible serpentine circuit board that was pre-torn out of the flexible substrate) and then feed this start end of the flexible serpentine circuit board into the wrapping field. For example, the yarn-processing machine can include a set of driven rollers aligned with an outlet of a magazine; once the flexible serpentine circuit board is loaded into the magazine, the yarn-processing machine can align the start end of the flexible serpentine circuit board with the set of driven rollers, drive these rollers into contact with the perforated substrate, and then activate the rollers to draw the flexible serpentine circuit board out of the flexible substrate and toward the outlet of the magazine. As the start end of the flexible serpentine circuit board reaches the wrapping field and is wrapped by fibers to form smart yarn, the yarn-processing machine can release these rollers from the flexible substrate to permit the yarn to continue to tear the flexible serpentine circuit board from perforations in the flexible substrate and to draw the flexible serpentine circuit board into the wrapping field, such as described above. The yarn-processing machine can also monitor tension on the flexible serpentine circuit board and can implement closed-loop controls to adjust the speed at which yarn is drawn out of the wrapping field in order to maintain tension on the flexible serpentine circuit board below a threshold force or strain and to reduce likelihood of breaking the flexible serpentine circuit board during this process.

Furthermore, in the foregoing implementations, the yarn-processing machine can monitor a proportion of the flexible serpentine circuit board remaining and can automatically load a second flexible serpentine circuit board—pre-separated from external regions of the flexible substrate or still intact—and transition to dispensing the start end of this second flexible serpentine circuit board into the wrapping field. For example, the yarn-processing machine can: load a second flexible serpentine circuit board into the magazine, wherein the second flexible serpentine circuit board defines a second set of sensing elements arranged along a serpentine trace, as described above; and then feed a start end of the second flexible serpentine circuit board into the wrapping field, such as in response to the preceding flexible serpentine circuit fully exiting the magazine and/or fully passing through the wrapping field. Therefore, the yarn-processing machine can implement methods described above for discrete sensing elements to sequentially drive start ends of flexible serpentine circuit boards into the wrapping field over time to produce a length of smart yarn significantly longer than the effective trace length of any one flexible serpentine circuit board in this variation.

However, the yarn-processing machine can be loaded with a flexible circuit board containing a serpentine or boustrophedonic trace and sensors in any other format or configuration in Block S210.

2.3 Yarn Processing

The second method S200 also includes: Block S220, which recites wrapping a set of fibers into a yarn within a wrapping field; Block S230, which recites feeding a leading end of a first sensing element, in the set of sensing elements, from the magazine into the wrapping field; Block S232, which recites releasing the first sensing element from the magazine into the wrapping field; and Block S234, which recites encasing the first sensing element between the set of fibers within the yarn. Generally, in Blocks S220, S230, S232, and S234, the yarn-processing machine combines a set of discrete fibers (e.g., natural spun fibers and/or continuous synthetic fibers) into a yarn and sequentially injects sensing elements at a juncture of these fibers such that these sensing elements are encased—in series—inside yarn exiting this juncture.

2.3.1 Wrapping Field and Wrapping Site

Generally, in Block S220, the yarn-processing machine draws multiple discrete fibers into a wrapping field and twists, spins, or otherwise combines multiple discrete fibers into yarn at a wrapping site (e.g., an eyelet), as shown in FIGS. 12 and 13. For example, a set of fiber bobbins, each containing a length of fiber, can be loaded into the yarn-processing machine ahead of the wrapping field; and a yarn bobbin can be loaded into the yarn-processing machine downstream from the wrapping field. Fibers from the set of fiber bobbins can be inserted into corresponding wrapping guides ahead of the wrapping field, passed through the wrapping site, wrapped around a driven friction spool, and connected to the yarn bobbin. When in operation, the yarn-processing machine can: rotate the friction spool to draw fibers from the fiber spools through their wrapping guides and through the wrapping site; actuate the wrapping guides to the twist, weave, or otherwise combine the fibers as (or before) the fibers pass through the wrapping site; and load yarn exiting the friction spool—and containing a series of sensing elements aligned and offset along the longitudinal axis of the smart yarn—onto the yarn bobbin in Block S220.

Therefore, in Block S220, the yarn-processing machine can: draw the set of fibers into the wrapping field in a first direction; join the set of fibers at or near a wrapping site within the wrapping field; then draw the yarn out of the wrapping field along the first direction; and collect this yarn on a bobbin or spool that can then be removed from the yarn-processing machine and loaded into a garment production machine (e.g., a numerically-controlled knitting machine) to produce a garment, as shown in FIG. 13.

Alternatively, yarn produced by the yarn-processing machine can be fed directly into such a garment production machine or a garment production component of the yarn-processing machine.

2.3.2 Sensing Element Wrapping

As these discrete fibers are fed into the wrapping field and combined to form yarn at the wrapping site, the yarn-processing machine can sequentially dispense sensing elements toward the wrapping site where these fibers are wrapped, spun, twisted, or otherwise combined around these sensing elements to form smart yarn. In particular, the yarn-processing machine can feed a leading end of a first sensing element in a first direction into the wrapping field ahead of the wrapping site and with the longitudinal axis of the first sensing element substantially parallel to this first direction in Block S230 such that the sensing element reaches the wrapping site substantially parallel to these fibers. As the leading end of the sensing element enters the wrapping site between multiple fibers simultaneously fed into the wrapping site and as the first sensing element passes through the wrapping site, the yarn-processing machine can wrap these fibers along the length of the first sensing element from its leading end to its second, opposite end in Block S232.

Once a sufficient length of the sensing element is wrapped within and supported by yarn exiting the wrapping site (e.g., at least 200 millimeters of 500-millimeter-long sensing element or at least 30% of the length of the sensing element), the magazine can release the sensing element, such as by retracting rollers or other features constraining the sensing element, in order to limit tension on the sensing element as the yarn draws the remainder of the sensing element into the wrapping site, thereby limiting opportunity for stretching, tearing, or breaking the sensing element. Similarly, the yarn-processing machine can monitor tension on the sensing element, such as mechanically or optically, and can automatically retract these rollers or other features constraining the sensing element when tension on the sensing element reaches a threshold tension indicating that the sensing element is sufficiently supported by the yarn.

In one implementation, the magazine (or other dispenser)—containing the set of sensing elements arranged in parallel—includes an outlet coaxially aligned with the wrapping site; and the yarn-processing machine can draw the set of fibers through fiber guides rotating about the outlet of the magazine ahead of the wrapping site, as described above and shown in FIG. 13. Alternatively, the magazine can be located remotely from the wrapping field and can include a tube or other feeder extending from the outlet of the magazine toward the wrapping site, as shown in FIG. 12. For example, the tube can terminate just ahead of the wrapping site, the yarn-processing machine can rotate the fiber guides about the tube, and the yarn-processing machine can draw fibers from the fiber guides past the end of the tube and into the wrapping site. In this example, to inject a new sensing element into the yarn, the yarn-processing machine can: load the sensing element into a receiver in the magazine; dispense the sensing element into the tube, such as mechanically or with a burst of air as shown in FIG. 12; and then force air through the tube toward the wrapping site in order to draw the sensing element from the magazine into the wrapping site when the sensing element is wrapped by the fibers and then mechanically drawn out of the tube by the yarn as the yarn exits the wrapping site.

2.3.3 Cored Yarn

In one implementation, the yarn-processing machine wraps (or twists, spins) fibers directly around a series of sensing elements. Alternatively, the yarn-processing machine can: arrange a set of packing fibers around these sensing elements and parallel to longitudinal axes of these sensing elements; and then wrap these packing fibers and sensing elements with wrapping fibers, as shown in FIG. 11. For example, as the yarn-processing machine drives a sensing element into the wrapping field, the yarn-processing machine can: draw a set of parallel packing fibers into the wrapping field to converge around the sensing element at the wrapping site; and wrap one or more wrapping fibers radially about the packing fibers and the sensing element—such as at or just behind the wrapping site—to form the yarn. In particular, by arranging packing fibers along a first conductive lead, a sensor, and a second conductive lead of a sensing element, the yarn-processing machine can produce a yarn that is more resistant to stretching when under tension, which may provide improved longitudinal support to the sensing element and thus reduce chances for the sensing element to break (e.g., a conductive lead to snap or a junction between a conductive lead and the sensor to fail) when the yarn is tensioned. Furthermore, these packing fibers and wrapping fiber may cooperate to provide increased radial support for the sensing element, thereby yielding a larger minimum bend radius of the yarn and the sensing element when worked and thus reducing opportunity for the conductive leads and junctions of the sensing element to fatigue and fail over time.

However, the yarn-processing machine can aggregate packing and/or wrapping fibers around a series of sensing elements in any other way to form the length of smart yarn in Block S234.

2.3.4 Fiber Materials

The yarn-processing machine can wrap the series of sensing elements with natural fibers, such as spun cotton or wool staple fibers, and/or with synthetic (e.g., polymeric) or natural continuous filaments, such as rayon, nylon, or silk. For example, the yarn-processing machine can: arrange continuous-filament packing fibers around a sensing element and extending parallel to the longitudinal axis of the sensing element; and wrap the sensing element and packing fibers with spun cotton fibers.

However, the yarn-processing machine can produce a length of smart yarn containing any other type or types of fibers arranged in any other way

2.4 Serial Sensing Elements

The second method S200 also includes: Block S240, which recites, in response to a trailing end of the first sensing element passing through the wrapping field following release of the first sensing element from the magazine into the wrapping field, feeding a leading end of a second sensing element, in the set of sensing elements, from the magazine into the wrapping field; Block S242, which recites releasing the second sensing element from the magazine into the wrapping field; and Block S244, which recites encasing the second sensing element between the set of fibers and longitudinally offset behind the first sensing element within the yarn. Generally, in Blocks S240, S242, and S244, the yarn-processing machine can repeat methods and techniques described above to feed a next sensing element into the wrapping field and to wrap fibers around this sensing element to continue the length of smart yarn; the yarn-processing machine can repeat this process continuously, until the length of smart yarn has reached a predefined target length, until a bobbin is fully loaded with the smart yarn, or until the magazine of sensing elements has been emptied.

In one implementation, the yarn-processing machine (or the magazine specifically) tracks the position of a preceding sensing element relative to the wrapping site and injects a next sensing element into the wrapping site at a predefined target distance behind the trailing end of the preceding sensing element. For example, the yarn-processing machine can feed the leading end of a second sensing element from the magazine into the wrapping field once the preceding sensing element has been fully encased by the yarn (e.g., downstream of the wrapping site) such that the leading end of the second sensing element is offset behind and is electrically isolated from the trailing end of the preceding sensing element. In this example, once the second sensing element is fully encased in the yarn, the yarn-processing machine can similarly: feed a leading end of a third sensing element from the magazine into the wrapping field such that the leading end of the third sensing element is offset behind and is electrically isolated from a trailing end of the second sensing element; release the third sensing element from the magazine into the wrapping field, such as once a sufficient length of the third sensing element is supported and/or constrained by the yarn; and then continue to pass fibers through the wrapping site to encase the third sensing element in the smart yarn. The first, second, third, and subsequent sensing elements can therefore be arranged in series, electrically isolated, and longitudinally offset by a static, preset distance from adjacent sensing elements within the resulting length of smart yarn.

Alternatively, the yarn-processing machine can inject sensing elements into the wrapping field in series such that adjacent conductive leads of these sensing elements are in contact with the resulting length of smart yarn, such as to achieve a higher density of sensors within the length of smart yarn.

Yet alternatively, the yarn-processing machine can serially inject sensing elements into the wrapping field at varying intervals. For example, the length of smart yarn can be designated for a particular garment or garment type of known size, knitting pattern, and sensor layout. In this example, a length of each run of smart yarn in the garment can be calculated based on the geometry of the garment and the sensor layout for the garment, and the yarn-processing machine can dynamically adjust relative positions at which sensing elements are injected into the wrapping field in order to achieve these lengths of smart yarn—each length containing one sensor—in a reverse-order from which these lengths of smart yarn will be incorporated into the garment during its manufacture. However, the yarn-processing machine can accommodate varying target lengths of the smart yarn in any other way.

2.5 Tensioning

In one variation, the yarn-processing machine tensions the smart yarn during production, such as between the spinning site and a bobbin, in order to strengthen and further align fibers in the yarn. Similarly, by tensioning the smart yarn and inducing tension in sensing elements in the smart yarn while fibers in the smart yarn are relaxed, the yarn-processing machine can produce a smart yarn that exhibits a reduced propensity for sensing elements contained therein to bunch. However, when tensioning the smart yarn, the yarn-processing machine can also: monitor a tensile force on the smart yarn and/or a strain on the smart yarn and can dynamically adjust tension on the smart yarn in order to maintain this tensile force and/or strain below a threshold, thereby limiting likelihood that the sensing element will break (or stretch sufficiently to alter resistance characteristics of its conductive leads).

For example, the yarn-processing machine can: tension the yarn between the wrapping field and the bobbin to elongate the set of fibers around sensing elements, in the set of sensing elements, now arranged within the yarn (e.g., by adjusting an angular speed of the bobbin relative to an output speed of smart yarn from the wrapping site); monitor a tension on the yarn (e.g., by optically tracking a width of the smart yarn or by applying an orthogonal force to the smart yarn between the wrapping site and the bobbin and measuring a later deflection distance); and maintain this tension in the yarn—between the wrapping field and the bobbin—below a preset break stress for these sensing elements, such as based on a junction type between conductive leads and sensors, a type of the conductive leads, and/or cross-sectional areas of conductive leads and/or sensors in the sensing elements.

However, the yarn-processing machine can tension the smart yarn in any other way and can implement any other closed-loop controls to achieve a target tension or stretch in the smart yarn while also limiting opportunity for a sensing element within the smart yarn to break or fail during this process.

2.6 Garment Production

As described above, the length of smart yarn can then be knit, woven, or otherwise incorporated into a garment, such as by the yarn-processing machine, by a local garment knitting apparatus (e.g., a numerically-controlled knitting machine), or remotely by another machine or process.

In one implementation, the bobbin—containing the length of smart yarn—is loaded into a garment knitting apparatus, such as manually or automatically. Similarly, a second bobbin—containing a length of a second yarn excluding sensing elements (i.e., a "standard" yarn)—is also loaded into the garment knitting apparatus. The garment knitting apparatus then draws the second yarn from the second bobbin, knits the second yarn into a garment, and interweaves segments of the smart yarn—each including one sensor and one sensing element—into the garment. The garment knitting apparatus, a manual operator, or a seamstress, etc. can then trim these segments of the smart yarn along their corresponding first and second conductive leads in order to expose these conductive leads; the conductive leads can then be installed in a connector or attached directly to a controller arranged or integrated into the garment.

For example, the garment knitting apparatus can combine the standard yarn with segments of the smart yarn—each containing all or a segment of a sensing element—to form a knitted garment in which these segments of smart yarn form loops in the garment and in which both ends of each segment of smart yarn terminate near a designated controller location on the garment. Once the garment is fully knitted, fibers surrounding these sensing elements can be trimmed or peeled back to expose the ends of these sensing elements, and the ends of these sensing elements can be inserted, bonded, soldered, or otherwise assembled into a connector that is then installed into a controller to complete assembly of the garment.

2.6.1 Sock

In one implementation shown in FIG. 13, the garment knitting apparatus knits the smart yarn and standard yarn into a sock, such as described above. For example, the garment knitting apparatus can: knit a multi-layer (e.g., two-layer) sock from the standard yarn; interweave—into the sole of the outer layer of the sock—a first segment of the smart yarn containing a first sensing element including a first temperature sensor; interweave—into the sole of the outer layer of the sock—a second segment of the smart yarn containing a second sensing element including a second temperature sensor offset from the first temperature sensor in the sole of the sock; and interweave—into the sole of the outer layer of the sock—a third segment of the smart yarn containing a third sensing element including a third temperature sensor offset from the first and second temperature sensors in the sole of the sock; etc. to incorporate six temperature sensors in the sole of the outer layer of the sock. The garment knitting apparatus can also: trim the first segment of the smart yarn along its first conductive lead and along its second conductive lead such that these conductive leads terminate proximal a pocket near the mouth and configured to receive a controller; trim the second segment of the smart yarn along its first conductive lead and along its second conductive lead such that these conductive leads terminate proximal the first and second conductive leads of the first sensing element; and trim the third segment of the smart yarn along its first conductive lead and along its second conductive lead such that these conductive leads terminate proximal the first and second conductive leads of the first and second sensing elements; etc. The first and second conductive leads of the first, second, third, etc. sensing elements can then be electrically coupled to a controller (e.g., to one power and sense channel pair per sensing element) that is then installed in the pocket before the pocket is sewn closed.

2.6.2 Sensor Location Check

In the variation described above in which a sensing element also includes a light element arranged adjacent the sensor and a second set of conductive leads extending from the light element parallel and adjacent the conductive leads extending from the sensor, conductive leads extending from a light element interwoven into the garment can be similarly connected to the controller (e.g., one power and one ground channel pair in the controller) or to an external testing device. With light elements in the sensing element arranged throughout the garment thus electrically coupled to the controller (or to an external testing device), the controller (or the external testing device) can supply power to these light elements via their conductive leads, thereby illuminating these light elements and visually indicating placement of these light elements—and therefore their sibling sensors—within the garment. A human or automated vision system can then visually inspect the garment with illuminated light elements to confirm that these light elements—and therefore their sibling sensors—are located within a threshold distance from target or nominal locations on the garment.

Therefore, once the garment is knitted or otherwise fabricated from a length of the smart yarn and a length of standard yarn, a human or other automated system can confirm a location of a sensor of a sensing element in the garment based on a location of a corresponding light element when illuminated by the controller (or by the external testing device) following manufacture of the garment. A human, the garment knitting apparatus, and/or another automated system can implement any other method or technique to power light elements in a garment thus produced in order to visually confirm locations of sensors integrated into the garment.

3. Third Method: Continuous Wire

Figure 14:
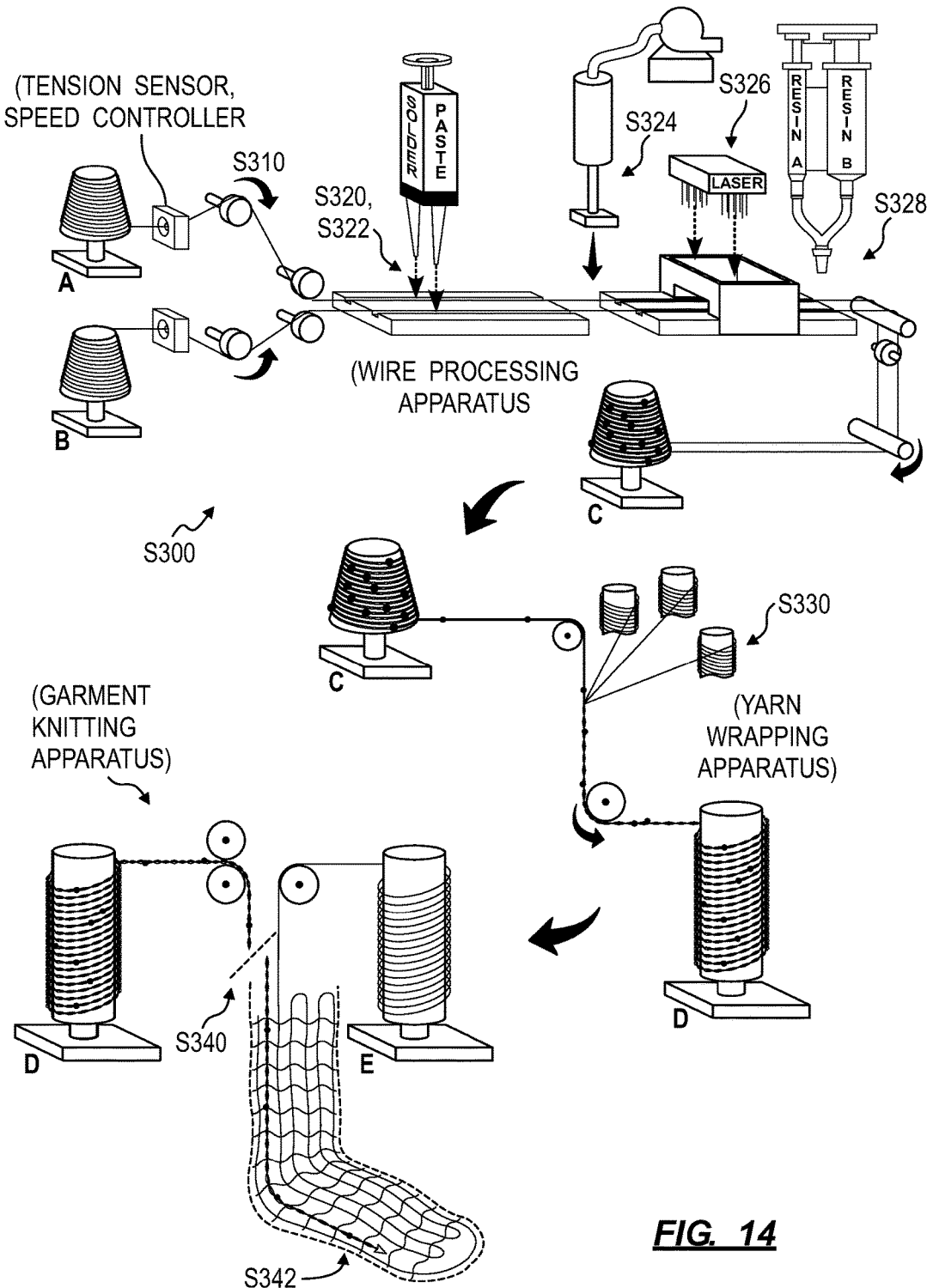
FIG. 14 is a flowchart representation of a third method.
Figure 15:
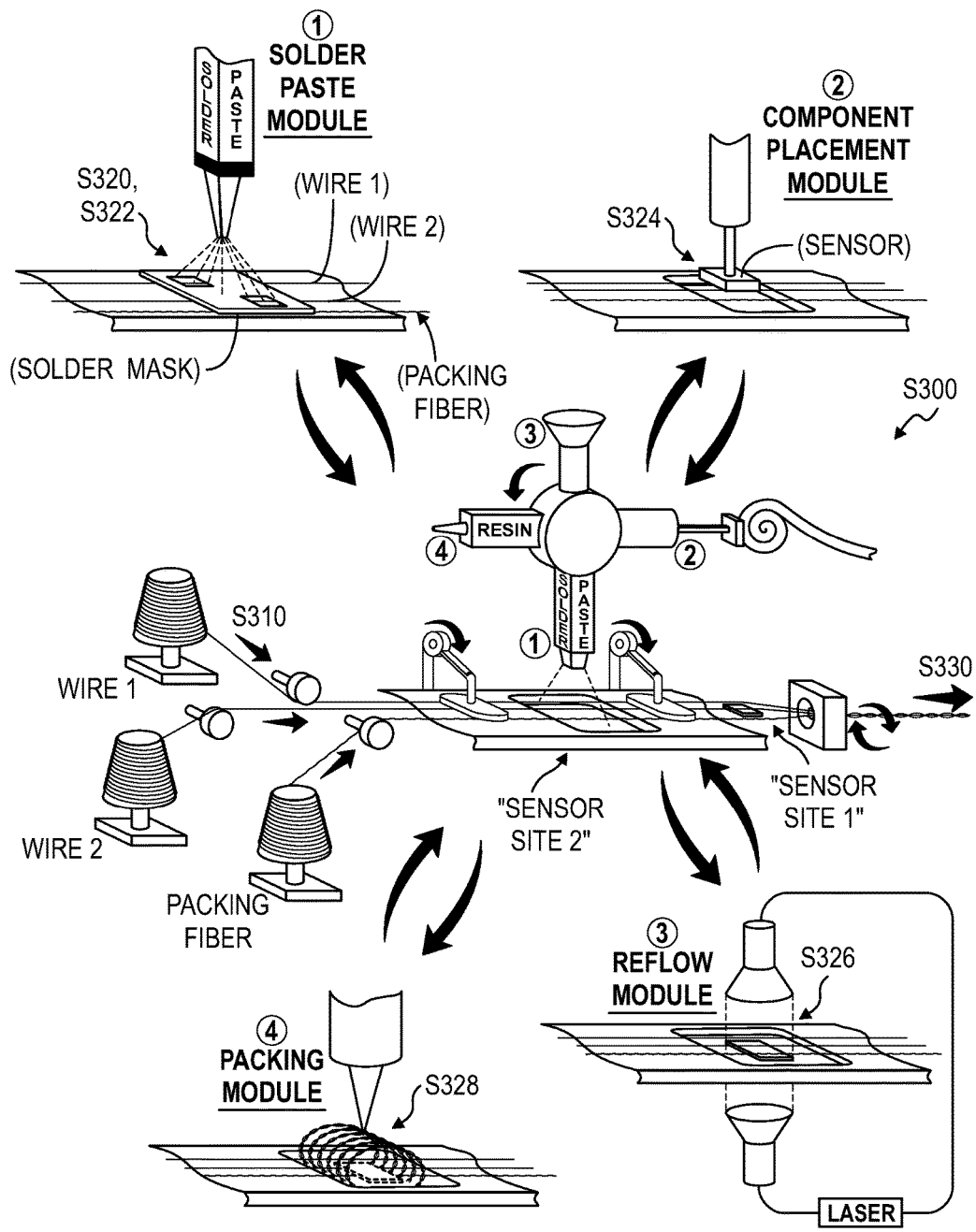
FIG. 15 is a flowchart representation of one variation of the third method.

As shown in FIGS. 14 and 15, the third method S300 for producing a smart yarn includes advancing a set of wires into an assembly field in Block S310, the set of wires including a first wire parallel and laterally offset from a second wire proximal the assembly field by a wire offset distance approximating a terminal offset distance. The third method S300 also includes, at each sensor site in a series of sensor sites longitudinally offset along the set of wires by a sensor offset distance and sequentially entering the assembly field: depositing a first volume of solder paste onto a first terminal location, on the first wire, coincident the sensor site in Block S320; depositing a second volume of solder paste onto a second terminal location, on the second wire, coincident the sensor site in Block S322; placing a sensor onto the set of wires at the sensor site in Block S324, the sensor including a first terminal in contact with the first volume of solder paste on the first wire and including a second terminal offset from the first terminal by the terminal offset distance and in contact with the second volume of solder paste on the second wire; and heating the set of wires within the assembly field to reflow the first volume of solder paste and the second volume of solder paste in Block S326. The third method S300 further includes: wrapping fibers around the set of wires and sensors arranged along the set of wires to form a continuous length of the smart yarn in Block S330; separating a first segment of the smart yarn from the continuous length of the smart yarn in Block S340; and weaving the first segment of the smart yarn into a garment in Block S342.

3.1 Applications

Generally, a system (e.g., a wire production apparatus) can execute the third method S300: to bring two insulated wires together at an offset distance approximating a distance between terminals of an electrical component (e.g., a sensor or a sensing element, as described above) within an assembly field; to selectively deposit solder paste onto these wires at a sensor site; to place the electrical component onto the wires with a first terminal of the electrical component in contact with solder paste on a first of these wires and with a second terminal of the electrical component in contact with solder paste on the second of these wires; to heat the wires and solder paste around the sensor site to reflow the solder paste, thereby attaching the sensor to the wires; to encapsulate the sensor and adjacent regions of the wires (whose insulating coatings may have been displaced by the solder paste when reflowed previously) with a potting or other insulative material; and to repeat this process to populate the set of wires with a sensor at each of a series of sensor sites longitudinally offset (e.g., by 50 centimeters) along the length of the set of wires (e.g., 2000 sensor sites along a 1000-meter length of wires). The wire production apparatus then wraps fibers (e.g., polymeric filaments and/or spun yarn of natural staple fibers) around the length of the set of wires and sensors, such as in real-time as sections of the wire and sensor assembly exit the assembly field, to form a continuous length (i.e., a long length) of smart yarn. The wire production apparatus can load the length of wire onto a bobbin, the bobbin can be loaded into a yarn wrapping apparatus, and the yarn wrapping apparatus can merge the wire and sensor assembly with fibers to form this continuous length of smart yarn.

Therefore, the wire production apparatus and/or the yarn wrapping apparatus can execute Blocks of the third method S300 to form a continuous (i.e., very long) wire assembly in which many sensors are in series arranged and offset along two parallel, insulated wires and in which these sensors are electrically connected in parallel between these two wires. This continuous wire assembly can be combined (e.g., wrapped or twisted) with textile fibers according to standard yarn production techniques to form a continuous length of smart yarn. In particular, because this wire assembly is substantially long (e.g., hundreds or thousands of meters in length), this wire assembly may lend itself well to wrapping with textile fibers to form a long length of smart yarn by existing large yarn processing equipment, which is generally configured to process long lengths of yarn continuously. This continuous length of smart yarn can then be cut between sensors, and these smart yarn segments—each containing one sensor—can then be woven into a garment As described above, the third method S300 can be executed to form a length of smart yarn that includes a series of temperature sensors (or sensors of any other type), and segments of this smart yarn can be woven into a garment to form a smart garment capable of measuring skin temperature of a user wearing the smart garment. For example, multiple segments of the smart yarn—each containing one touch sensor—can be woven into the sole of a sock; when the sock is worn on a user's foot, a controller integrated into the sock and connected to these segments of smart yarn can measure temperatures across the sole of the user's foot, which may then be analyzed to detect sores, infections, or other abnormalities occurring in the user's foot over time, such as described in U.S. patent application Ser. No. 15/382,248.

3.2 Wires and Packing Fiber

Block S310 of the third method S300 recites advancing a set of wires into an assembly field, wherein the set of wires includes a first wire parallel and laterally offset from a second wire proximal the assembly field by a wire offset distance approximating a terminal offset distance. Generally, in Block S310, the wire production apparatus or other system executing the third method S300 dispenses two (or more) wires forward to locate a sensor site on these wires within an assembly field in preparation for dispensing solder paste onto the sensor site on these wires in Blocks S120 and S122, placing a sensor or other electrical component onto the solder paste in Block S124, reflowing the solder paste in Block S126, etc.

In one implementation shown in FIG. 14, an input side of the wire production apparatus is loaded with a first input spool containing a length of a first wire and is loaded with a second input spool containing a length of a second wire. In this implementation, an output side of the wire production apparatus includes a driven spool (or bobbin). During setup, the first ends of wires on the first and second input spools are passed through the assembly field—such as through various guides within and outside of the assembly field—and connected to the driven spool. During operation, the wire production apparatus can drive the driven spool forward to unwind wire from the first and second input spools and to serially draw sensor sites on the wires through the assembly field. The wire production apparatus can also include a set of fixed linear guides and/or rotating guides arranged between the input spools and the driven spool and configured to locate the wires within the assembly field. For example, the wire production apparatus can locate the first and second wires parallel and linearly offset by a target distance within the assembly field in Block S310 in preparation for placing a sensor onto these wires such that the terminals of the sensor are centered over corresponding volumes of solder paste applied to these wires. In this example, the target distance can approximate a known offset distance between the terminals of the sensor.

As shown in FIG. 14, The wire production apparatus can further include wire tension sensors between the input and driven spools, and the wire production apparatus can adjust the speed of the driven spool to maintain the tension on the wires below a threshold tension, such as a static threshold tension or a dynamic threshold tension that is inversely proportional to temperatures of the wires. The wire production apparatus can also include a linear encoder or other position sensor configured to output a signal based on a length of wire that has passed through the assembly field, and the wire production apparatus can track sensor sites along the wires based on outputs of this position sensor.

As described below, the wire production apparatus can advance the set of wires through the assembly field continuously in Block S310; and the wire production apparatus can include solder paste, component placement, reflow, and/or packing material models configured to track (i.e., move) with sensor sites on the wires as the wires move through the assembly field. Alternatively, the wire production apparatus can intermittently index the wires forward into the assembly field in Block S310, such as: by advancing each sensor site on the wires forward from one module to the next; or by advancing one sensor site into the assembly field, moving the modules into position over the sensor site until the sensor site is completed, and then advancing the wire forward to locate the next sensor site in the assembly field.

As described below, the wire production apparatus can feed multiple wires into the assembly field to mount one or more electrical components at each of multiple longitudinally-offset sensor sites along the wires. For example, the wire production apparatus can process a set of wires, each of which includes an electrically-conductive core (e.g., between 0.01 and 0.1 millimeter in diameter) and an insulative coating over the electrically conductive core.

In one variation, the wire production apparatus combines the set of wires with a packing fiber, such as described above and as shown in FIG. 15. For example, the wire production apparatus can simultaneously feed the set of wires and a packing fiber into the assembly field such that the packing fiber, the first wire, and the second wire are parallel and laterally offset within the assembly field (e.g., proximal the sensor site in the assembly field).

However, the wire production apparatus can implement any other methods or techniques to feed the set of wires (and the packing fiber(s)) into the assembly field in Block S310.

3.3 Solder Paste

The third method S300 includes Blocks S320 and S322, which recite, at each sensor site in a series of sensor sites longitudinally offset along the set of wires by a sensor offset distance and sequentially entering the assembly field, depositing a first volume of solder paste onto a first terminal location—on the first wire—coincident the sensor site and depositing a second volume of solder paste onto a second terminal location—on the second wire—coincident the sensor site. Generally, in Block S320 and S322, the wire production apparatus applies a volume of solder paste—sufficient to bond a terminal of the sensor to the corresponding wire—onto each wire at a sensor site currently occupying the assembly field; and repeats this process for each subsequent sensor site that enters the assembly field.

In one implementation shown in FIG. 15, the wire production apparatus includes a solder paste module that executes Blocks S320 and S322. In this implementation, the solder paste module can include: a solder mask defining a set of perforations patterned according to a terminal arrangement of sensors scheduled for installation on the wires; and a solder paste sprayer configured to spray solder paste through the perforations in the solder mask and onto the wires. For example, the solder mask can include a thin planar card arranged over an opening in the assembly field; the solder paste sprayer can be arranged over the card opposite the opening; and the assembly field can define two parallel guide tracks intersecting the opening. The wire production apparatus can draw the first and second wires along these parallel guide tracks in Block S310 to align the wires to perforations in the solder mask (or move the solder mask and solder paste sprayer to align perforations in the solder mask to the wires) within the assembly field. When a next sensor site on the wires is aligned with the opening, the wire production apparatus can stop the wires and trigger the solder paste sprayer to spray solder paste toward the card before moving the wires forward to align the sensor site to a component placement module (or before replacing the solder paste module with a component placement module).

In another example, the solder paste module can include a wheel configured to ride on the wires (or vice versa) and defining a circumference that is an integer multiple of the sensor offset distance specified for the smart yarn. As the wheel rotates and a designated sensor site on the wires approaches the wheel, the solder paste module can brush sensor paste onto a designated paste application section of the face of the wheel; the wires can thus collect solder paste at the sensor site as the wires contact this paste application section of the wheel. The wire production apparatus can then move the sensor site of the wire off of the wheel and to a next location within the assembly field to receive a sensor. Alternatively, the wire production apparatus can place the sensor onto the wires directly over the paste application section of the wheel.

In yet another example, the solder paste module can include one or more solder paste pens; as a next sensor site on the wires enters the assembly field, the solder paste module can advance the solder paste pens forward and into contact with the wires, thereby applying solder paste to the wires at at the designated sensor site.

In another example, the solder paste module can similarly include a roller, can coat the roller with solder paste, and can roll the roller laterally across the wires as the sensor site passes the roller. In this example, the solder paste module: can include a perforated mask, as described above; can locate the solder mask between the wires and the roller; and can roll the roller across the solder mask to selectively deposit solder paste onto the wires through the solder mask.

However, the wire production apparatus can include a solder paste module of any other form and configured to dispense solder paste onto the wires at a sensor site in any other way.

3.4 Sensor Placement

Block S324 of the third method S300 recites, at each sensor site in the series of sensor sites along the set of wires, placing a sensor onto the set of wires at the sensor site. Generally, in Block S324, the wire production apparatus can place a sensor (or other electrical component or sensing element) onto a sensor site on the set of wires such that a first terminal of the sensor contacts the first volume of solder paste on the first wire and a second terminal of the sensor— offset from the first terminal by a terminal offset distance— contacts the second volume of solder paste on the second wire; and repeats the process at subsequent sensor sites along the set of wires. In particular, a sensor defines a sensor footprint with terminals offset by a known distance; the wire production apparatus can therefore offset the first and second wires by (approximately) this same offset distance as a component placement module depresses the sensor into solder paste coating these wires at a sensor site.

In one implementation, the component placement module includes a suction wand and a component dispenser and implements pick-and-place techniques to retrieve a component from the component dispenser, move the suction wand over the component site on the wires, and then extend the suction wand toward the sensor site to place the sensor onto the wires with terminals of the sensor contacting volumes of solder paste on corresponding wires, as shown in FIGS. 14 and 15. In this implementation, the assembly surface can define an opening below the wires opposite the component placement module; the component placement module can thus extend the suction wand into a sensor site such that the wires deflect downward into the opening, thereby ensuring that the sensor is sufficiently depressed into the solder paste while reducing opportunity for solder paste on the wires to weep onto and contaminate the assembly surface.

The component placement module can additionally or alternatively include a backing surface configured to support the back of the wires as the suction wand depresses a sensor onto a sensor site. For example, as the component placement module advances the suction wand forward to place a sensor onto the wires, the component placement module can also advance the backing surface—perpendicular to the wires and parallel to the suction surface—to support the wires as the sensor is depressed onto the wires. Once the sensor is placed onto the sensor site, the component placement module can retract the backing surface before advancing the wires forward to prevent deposition of solder paste onto the backing surface.

In the foregoing example, the solder paste module can also dispense solder paste onto the backing surface (e.g., a planar surface or two prongs offset by the terminal offset distance of the sensor) rather than onto the wires directly; then, as the suction wand moves a sensor toward the wires, the component placement module can move the backing surface up to support the wires and to deposit solder paste from the backing surface onto the wires; once the backing surface and the sensor meet the wires, the component placement module can retract the backing surface and the suction wand to yield a discrete volume of solder paste coating the wires and loosely bonded to terminals of the sensor at the sensor site.

However, the component placement module and the wire production apparatus generally can implement any other method or technique to place a sensor on the wires at a sensor site in Block S324. The component placement module can repeat this process at each sensor site along the length of the wires.

3.5 Reflow

Block S326 of the third method S300 recites, at each sensor site in the series of sensor sites along the set of wires, heating the set of wires within the assembly field to reflow the first volume of solder paste and the second volume of solder paste. Generally, in Block S326, a reflow module in the wire production apparatus heats the wires locally at a sensor site to reflow the solder paste in order to fuse each terminal of the sensor to its corresponding wire.

As described above, each wire includes an electrically-conductive core and an insulative coating; and the solder paste module applies solder paste directly to the insulative coating of the wires at each sensor site in Block S320 and S322. (In particular, the solder paste module can: deposit the first volume of solder paste over the insulative coating on the first wire at the first terminal location; and deposit the second volume of solder paste over the insulative coating on the second wire at the second terminal location.) In this implementation, the reflow module can heat the first volume of solder paste on the first wire in order to: burn the insulative coating off of the first wire at (and around) the first terminal location on the first wire; reflow the first volume of solder paste; and thus bond the first volume of solder paste to the electrically-conductive core of the first wire at the first terminal location and to the first terminal of the sensor. Simultaneously, the reflow module can heat the second volume of solder paste to: burn the insulative coating off of the second wire at the second terminal location; reflow the second volume of solder paste; and thus bond the second volume of solder paste to the electrically-conductive core of the second wire at the second terminal location and to the second terminal of the sensor.

In one implementation, the reflow module includes a laser-based heater and an insulated heater box, as shown in FIG. 14. To reflow the solder paste, the reflow module: locates the heater box (defining an insulated volume) over the component site; and then selectively projects an energy beam (e.g., a laser beam) onto the first volume of solder paste and the second volume of solder paste in order to reflow these volumes of solder paste.

The reflow module can also include a cooling unit, such as a blower, configured to blow (cooled) air across the sensor site once the solder paste has reached a reflow temperature in order to cool the wires, sensor, and solder before the wires are tensioned to move the assembly forward through the assembly field.

Alternatively, the reflow module can include: an infrared heater facing the wires; and a reflective surface facing the wires opposite the infrared heater and configured to reflect energy back toward the wires during a reflow cycle. However, the reflow module can include a heating element of any other type, a reflective surface, and/or an insulated volume of any other form, all of which can cooperate in any other way to reflow solder paste on the wires to attach a sensor to the component site.

(In one variation: the wires are uncoated; and the solder paste module coats the full length of the wires exiting the solder paste module; the reflow module focuses energy locally to a sensor site to reflow solder paste only around sensors placed on these wires; the wire is passed through a scraper or chemical stripper to remove loose solder paste, which may then be recycled back into the solder paste module; and the full length of the wires are then coated with an insulative coating before being brought into contact, such as by twisting, and before being wrapped with a filament in Block S330.)

3.6 Tension Control

In one variation, the wire production apparatus monitors tension on the wires—such as a function of temperature of the wires—in order to limit likelihood of breaking the wires. In particular, the wire production apparatus can tension the set of wires to draw the wires off of their spools and into the assembly field. Once solder paste and a sensor has been applied to a sensor site on the wires in Blocks S320, S322, and S324, the wire production apparatus can: reduce tension on the set of wires across the sensor site in preparation for heating the set of wires; heat the set of wires to reflow the first volume of solder paste and the second volume of solder paste; and then increase tension on the set of wires to draw the sensor site out of the assembly field once the set of wires at the first sensor site have cooled to below a threshold temperature. For example, the reflow module can include an infrared or other remote temperature sensor, can monitor the temperature of the wires at the sensor site, cease heating the sensor site once this temperature has reached a preset reflow temperature designated for the solder paste, and then enable re-tensioning of the wires only once their measured temperature has dropped below a predefined tension temperature in order to minimize possibility of breaking the wires or stretching the wires, which may reduce their cross-section, increase their electrical resistance, and thus affect measurement from the sensor at the sensor site.

To constrain the wires proximal a sensor site during Blocks S320, S322, S324, and/or S326, the wire production apparatus can clamp or otherwise constrain the wires onto an assembly surface, as shown in FIG. 15. For example, the wire production apparatus can include: a first actuatable clamp—such as a pneumatic or electromechanical clamp—arranged across an entry side of the assembly surface; and a second actuatable clamp arranged across an exit side of the assembly surface. In this example, the wire production apparatus can: advance the set of wires forward to locate a first sensor site on the set of wires over an assembly surface within the assembly field in Block S310; and trigger the first clamp and the second clamp to close, thereby binding the set of wires against the assembly surface once the sensor surface is located in a target position within the assembly field, such as adjacent the solder paste module. Once a first sensor is assembled onto the first sensor site on the set of wires in Block S324, the solder paste is reflowed and then cooled in Block S326, and the first sensor site is encased in packing material in Block S328, the wire production apparatus can: trigger the first clamp and the second clamp to open, thereby releasing the set of wires from the assembly surface; and then advance the set of wires forward to locate a second sensor site—offset behind the first sensor site by an integer multiple of the sensor offset distance—on the set of wires over the assembly surface before repeating the foregoing process to assemble additional sensors onto corresponding sensor sites along the wire. The wire production apparatus can therefore constrain the wire on each side of a sensor site while a sensor is installed on this sensor site in order to preserve the length of the wire on each side of the sensor site, to prevent the wires from moving laterally relative to one another during a reflow cycle, and to reduce opportunity for the wires to break from excess tension. In this implementation, the wire production apparatus can: move the assembly surface—and clamps constraining the wires onto the assembly surface—from the solder paste module through to the packing module; or sequentially move the solder paste module, component placement module, reflow module, and packing module, etc. into position over a sensor site in order to assemble a sensor onto the sensor site, as described below.

However, the wire production apparatus can implement any other method or technique: to monitor and control tension on segments of the wires passing through the assembly field; and to constrain the wires proximal a sensor site as the wire production apparatus installs a sensor over this sensor site.

3.7 Packing Material

In one variation shown in FIGS. 14 and 15, the third method S300 further includes Block S328, which recites, for each sensor site along the set of wires, depositing a packing material over the sensor, the first terminal location on the first wire, and the second terminal location on the second wire. Generally, in Block S328, a packing module in the wire production apparatus can deposit a packing material—such as an insulative photo-curable epoxy resin—over a sensor site on the wires in order to: prevent shorting between wires where the insulative coating was removed adjacent the sensor site during a reflow cycle; to provide additional support the wires where temperature cycling may have increased brittleness of the wires; and to provide further support to the connection between the sensor and the wires at the sensor site.

For example, the packing module can include a resin reservoir, a nozzle (or dropper) fluidly coupled to the resin reservoir, an actuator configured to drive the nozzle forward toward the set of wires to dispense a metered volume of resin onto the sensor site, and an optical emitter configured to illuminate—and thus cure—the metered volume of resin. However, the packing module can implement any other methods or techniques, such as described above, to serially dispense packing material onto each sensor site along the set of wires.

In one implementation, the wire production apparatus: advances the set of wires forward to locate a first sensor site on the set of wires in the assembly field in Block S310; deposits a first volume of solder paste onto a first terminal location at the first sensor site on the first wire in Block S320; deposits a second volume of solder paste onto a second terminal location at the first sensor site on the second wire in Block S322; places a first sensor onto the set of wires at the first sensor site in Block S324; heats the set of wires proximal the first sensor site to reflow the solder paste, thereby bonding the first sensor to the set of wires at the first sensor site in Block S326; deposits a first volume of packing material—including a curable resin—around the first sensor in Block S328; and then advances the set of wires forward to locate a second sensor site—offset behind the first sensor site by the sensor offset distance—on the set of wires in the assembly field once the first volume of packing material has sufficiently cured. The wire production apparatus can therefore stop motion of the set of wires until a volume of resin deposited onto a sensor site has been cured.

In the implementation described above in which the wire production apparatus combines the set of wires with a packing fiber, the wire production apparatus can bring a local segment of the packing fiber into the immediate vicinity of or in direct contact with a sensor site once a sensor has been installed on this sensor site and once the wires, solder, and sensor have reached a temperature below a preset threshold temperature. With the sensor site and local segment of the packing fiber now bunched, the packing module can deposit the volume of packing material over the sensor site and local segment of the packing fiber in order to locally bond the packing fiber to the sensor site (in addition to encasing the sensor and terminal locations on the set of wires). In particular, the packing module can deposit the volume of packing material over the sensor, adjacent local regions of the set of wires, and the local segment of the packing fiber in order to intermittently bond the packing fiber to the set of wires, which may thus support segments of the wires between adjacent sensor sites from stretching and breaking under tension, such as both before and after the wires and sensors are wrapped with wrapping fibers in Block S330.

However, the wire production apparatus can implement any other method or technique to deposit and cure packing material around each sensor site along the set of wires.

3.8 Second Electrical Component

In one variation, the wire production apparatus processes three or more discrete wires and assembles multiple electrical components onto these wires in Blocks S310, S320, S322, and S324, etc. For example, the wire production apparatus can advance the set of wires—including the first wire, the second wire, and the third wire—into the assembly field in Block S310, wherein the third wire is parallel and laterally offset from the second wire opposite the first wire within the assembly field. In this example, the second wire can be centered between the first and third wires and offset from these wires by the wire offset distance described above. In this example, the solder paste module can: deposit a first volume of solder paste onto a first terminal location, on the first wire, coincident a sensor site; deposit a second volume of solder paste onto a second terminal location, on the second wire, coincident the sensor site; deposit a third volume of solder paste onto a third terminal location, on the third wire, coincident the sensor site; and deposit a fourth volume of solder paste onto a fourth terminal location, adjacent the second terminal location on the second wire, coincident the sensor site in Blocks S320 and S322. The component placement module can then: place the sensor into the first and second volumes of solder paste, as described above; and place a second electrical component onto the set of wires at the sensor site, wherein the electrical component includes a third terminal in contact with the third volume of solder paste on the third wire and includes a fourth terminal offset from the third terminal by the terminal offset distance and in contact with the fourth volume of solder paste on the second wire. The reflow module can then heat the first, second, and third wires and the sensor and electrical component to reflow these four discrete volumes of solder paste in Block S326, thereby bonding the sensor to the first and second wires and bonding the electrical component to the second and third wires at the sensor site.

In the foregoing example, the electrical component can include a light element, and the sensor can include a temperature sensor, such as described above. When a segment of the resulting smart yarn—including one sensor site—is woven into a garment: the second wire can be connected to a power supply in the garment and thus supply power to the light element and to the temperature sensor; the first wire can be connected to an analog input at which the voltage across the temperature sensor is measured, which may then be transformed into a voltage at the temperature sensor; and the third wire can be connected to a switched ground terminal to selectively activate and deactivate the light element. In this example, the location of the temperature sensor—contained in the segment of the smart yarn thus woven into the garment—can be determined based on the location of the corresponding light element in the garment when the ground terminal is closed and the light element thus illuminated.

However, in this implementation, the wire production apparatus can process any other number of wires and can install any other number or type of sensors or other electrical components onto these wires in Blocks S310, S320, S322, and S324, etc.

3.9 Dynamic Modules

In one variation shown in FIG. 15, the wire production apparatus includes movable (or "dynamic") solder paste, component placement, reflow, and packing modules and selectively advances these modules into position over a sensor site on the set of wires in order to install a sensor (and/or other electrical component) onto this sensor site in Blocks S320, S322, S324, S326, and S328. For example, the wire production apparatus can feed the set of wires into the assembly field and clamp the set of wires to a fixed assembly surface with a designated sensor site on the wires aligned to an assembly zone on the assembly surface in Block S310, as described above. In this example, the solder paste, component placement, reflow, and packing modules can be arranged on a linear or rotary turret over the assembly surface, and the wire production apparatus can: advance the solder paste module into position over the sensor site to deposit the first volume of solder paste onto the first wire in Block S320 and to deposit the second volume of solder paste onto the second wire in Block S322; advance the component placement module into position over the first sensor site to place a first sensor onto the set of wires at the first sensor site; advance the reflow module into position over the first sensor site to heat the set of wires proximal the first sensor site in Block S326; and then advance the packing module into position over the first sensor site to encase the first sensor in resin in Block S328. Once the resin has dried or cured, the wire production apparatus can release the set of wires from the fixed assembly surface and then advance the set of wires forward to locate a second sensor site—offset behind the first sensor site by the sensor offset distance—on the set of wires over the fixed assembly surface.

3.10 Static Modules

Alternatively, the foregoing modules can be arranged in fixed positions within the wire production apparatus, and the wire production apparatus can sequentially align a sensor site on the set of wires with each module as the wires are fed through the assembly field, as shown in FIG. 14.

In one implementation, the wire production apparatus draws the wires over a fixed assembly surface. For example, the fixed assembly surface can define a planar surface extending across each module and defining opens below each module as described above. Alternatively, the fixed assembly surface can define a set of grooves or channels that extend from ahead of the solder paste module to just ahead of the component placement module; the wire production apparatus can thus draw each wire through its corresponding channel up to the component placement module, at which point a sensor is placed onto and spans the wires. Alternatively, the wire production apparatus can include a movable assembly surface, can clamp the set of wires to the movable assembly surface, as described above, and can move the assembly surface along the series of fixed modules to assemble a sensor onto a sensor site coincident the assembly surface in Blocks S320, S322, and S324, etc.

In this variation, the wire production apparatus can intermittently advance and pause the set of wires (e.g., the assembly surface clamped to the set of wires) in Blocks S320, S322, and S324, etc. For example, the wire production apparatus can: sequentially advance the assembly surface—clamped to the set of wires and spanning a first sensor site—from the solder paste module in Blocks S320 and S322 to the component placement module in Block S324 to the reflow module in Block S326, etc. Once installation of a sensor on this first sensor site is complete, the wire production apparatus can: release the wires from the assembly surface; retract the assembly surface to locate a second sensor site on the set of wires over the assembly surface; and trigger the clamps on the assembly surface to reengage the set of wires before repeating the foregoing process to assemble a sensor onto the second sensor site. In this example, the wire production apparatus can include multiple discrete assembly surfaces and can cycle these assembly surfaces linearly from the entry of the assembly field to the exit and back again to the entry of the assembly field as sensor sites along the set of wires are completed.

Alternatively, the wire production apparatus can include a rotary wheel in which the outer flange of the rotary wheel defines the assembly surface; and the module can be arranged about the perimeter of the wheel such as from a 0° position at which the set of wires enter the rotary wheel to a 180° position at which the set of wires exit the rotary wheel. In this example, the wire production apparatus can feed the set of wires onto the outer flange of the rotary wheel; once a next sensor site contacts the outer flange and reaches a 5° position on the wheel, the solder paste module can deposit solder paste onto the wires in Block S320 and S322. As the wheel rotates and the sensor site enters the 30° position, the component placement module can place a sensor onto this sensor site. Once the sensor site enters the 60° position, the reflow module can reflow the solder paste, and the wires, solder, and sensor can cool from the 60° to the 120° position. At the 120° position, the packing module can deposit packing material onto the sensor site, and the packing material can cure from the 120° to the 180° position at which this sensor site lifts off of the outer flange and at which a next sensor site lands on the outer flange. The wire production apparatus can then repeat this process for the next sensor site. (The circumference of the rotary wheel at the outer flange can therefore equal twice the sensor offset distance between adjacent sensor sites along the set of wires.)

The wire production apparatus can therefore intermittently or continuously move a sensor site on the set of wires through the assembly field past static modules. Alternatively, the wire production apparatus can continuously move a sensor site on the set of wires through the assembly field and can synchronize movement of each module with the sensor site as the module performs its corresponding task on the sensor site.

However, the wire production apparatus can implement any other methods or techniques to assemble a sensor onto a sensor site on the set of wires in Blocks S310, S320, S322, S324, etc.

3.11 Wrapping

Block S330 of the third method S300 recites wrapping fibers around the set of wires and sensors arranged along the set of wires. Generally, in Block S330, the wire production apparatus (or a separate yarn wrapping apparatus) wraps fibers—such as polymeric filaments and/or spun yarn of natural staple fibers, as described above—around the set of wires and sensors to form a continuous length of the smart yarn that contains a series of sensors longitudinally offset along the length of the smart yarn and connected in parallel between the first wire and the second wire, shown in FIG. 14. In particular, in Block S330, the wire production apparatus can implement methods and techniques described above to wrap a synthetic or natural fiber around the continuous length of wire to form an assembly with the feel of a textile but that can be connected to a controller to collect sensor data. For example and as described above, the wire production apparatus can arrange packing fibers longitudinally along the length of the set of wires in Block S310; radially twist the packing fibers and the set of wires; and then wrap wrapping fibers radially about the set of wires, sensors, and the packing fibers in Block S330.

In one variation shown in FIG. 14, the wire production apparatus winds the set of wires and sensors—arranged on sensor sites exiting the assembly field—onto a first bobbin. Once the first bobbin is fully loaded (or a spool of wire from which the wires are fed into the assembly field is emptied), the first bobbin can be loaded into a yarn wrapping apparatus. The yarn wrapping apparatus can then: wrap spun yarn of natural staple fibers and/or synthetic filaments around the set of wires and sensors to produce a length of the smart yarn separate from the wire production apparatus; and then wind the length of the smart yarn onto a second bobbin. This second bobbin can then be loaded into a separate garment knitting apparatus, as described above, to produce a garment. Therefore, in this implementation, the wire production apparatus can produce a continuous length of "smart wire" intermittently populated with sensors; the yarn wrapping apparatus can wrap the continuous length of smart wire with wrapping fibers to produce a continuous length of "smart yarn;" and the garment knitting apparatus can combine segments of this smart yarn with a standard yarn or textile to produce a "smart garment," as described above.

Alternatively, the wire production apparatus can wrap the smart wire with wrapping fibers and/or weave the resulting smart yarn into a garment locally.

3.12 Garment Production

As shown in FIG. 14, one variation of the third method S300 includes: Block S340, which recites separating a first segment of the smart yarn from the continuous length of the smart yarn; and Block S342, which recites weaving the first segment of the smart yarn into a garment. Generally, in Blocks S340 and S342, the wire production apparatus or separate garment knitting apparatus integrates sections of the smart yarn into a garment to produce a smart garment.

In one implementation, the garment knitting apparatus: separates a segment of the smart yarn—containing a segment of the first wire, a segment of the second wire, and a single sensor coupled to the segment of the first wire and to the segment of the second wire—from the continuous length of the smart yarn; knits a length of a second yarn—excluding wires and sensors—into a garment; and interweaves the segment of the smart yarn into the garment with a first end of the segment of the smart yarn terminating proximal a controller junction in the garment, as shown in FIGS. 13 and 14. A controller can then be installed on the garment near the controller junction; the wrapping fibers can be peeled back from the first end of the smart yarn to expose the first and second wires; the wires can be distinguished by color of their insulative coatings; and the exposed ends of the first and second wires can be connected to their corresponding terminals on the controller.

For example, the wire production apparatus can install temperature sensors on sensor sites along the set of wires in Block S324. The garment production can then: knit the length of the second yarn into a sock; cut a segment of the smart yarn containing a single temperature sensor from the continuous length of the smart yarn in Block S340; and interweave the segment of the smart yarn into the sock with the first end of the segment of the smart yarn terminating proximal an opening of the sock and with the single temperature sensor located in a sole of the sock in Block S342, such as described above.

However, the wire production apparatus, the yarn wrapping apparatus, and/or the garment production apparatus can implement any other method or technique to prepare a length of smart yarn and to incorporate this length of smart yarn into a garment of any other type.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for producing a smart yarn, the method comprising:
    advancing a set of wires into an assembly field along a longitudinal direction, the set of wires comprising a first wire parallel and laterally offset from a second wire by a wire offset distance approximating a terminal offset distance;
    at each sensor site in a series of sensor sites longitudinally offset along the set of wires extending in the longitudinal direction by a sensor offset distance and sequentially entering the assembly field as the set of wires is advanced into the assembly field:
        depositing a first volume of solder paste onto a first terminal location, on the first wire, coincident the sensor site;
        depositing a second volume of solder paste onto a second terminal location, on the second wire, coincident the sensor site;
        placing a sensor onto the set of wires at the sensor site, the sensor comprising a first terminal in contact with the first volume of solder paste on the first wire and comprising a second terminal offset from the first terminal by the terminal offset distance and in contact with the second volume of solder paste on the second wire; and
        heating the set of wires within the assembly field to reflow the first volume of solder paste and the second volume of solder paste; and
    wrapping fibers around the set of wires and sensors arranged along the set of wires to form a continuous length of smart yarn.

2. The method of claim 1, wherein wrapping fibers around the set of wires and sensors comprises wrapping fibers around the set of wires and sensors to form the continuous length of the smart yarn containing a series of sensors longitudinally offset along the length of the smart yarn and connected in parallel between the first wire and the second wire.

3. The method of claim 2, further comprising:
    separating a segment of the smart yarn from the continuous length of the smart yarn, the segment of the smart yarn comprising a segment of the first wire, a segment of the second wire, and a single sensor coupled to the segment of the first wire and to the segment of the second wire;
    knitting a length of a second yarn into a garment, the second yarn excluding wires and sensors;
    interweaving the segment of the smart yarn into the garment with a first end of the segment of the smart yarn terminating proximal a controller junction in the garment; and connecting a first end of the segment of the first wire and a first end of the segment of the second wire, at the first end of the segment of the smart yarn, to terminals of a controller coupled to the garment at the garment junction.

4. The method of claim 3:
wherein placing a sensor onto the set of wires at each sensor site along the set of wires comprises placing a temperature sensor onto the set of wires at each sensor site along the set of wires;
wherein knitting the length of the second yarn into the garment comprises knitting the length of the second yarn into the garment comprising a sock;
wherein separating the segment of the smart yarn from the continuous length of the smart yarn comprises cutting the segment of the smart yarn comprising a single temperature sensor from the continuous length of the smart yarn; and
wherein interweaving the segment of the smart yarn into the garment comprises interweaving the segment of the smart yarn into the sock with the first end of the segment of the smart yarn terminating proximal an opening of the sock and with the single temperature sensor located in a sole of the sock.

5. The method of claim 1:
wherein advancing the set of wires into the assembly field comprises advancing the set of wires into the assembly field in a wire production apparatus;
further comprising:
at the wire production apparatus, winding the set of wires and sensors arranged along the set of wires onto a first bobbin; and
loading the first bobbin into a yarn wrapping apparatus;
wherein wrapping fibers around the set of wires and sensors comprises, at the yarn wrapping apparatus:
wrapping spun yarn of natural staple fibers around the set of wires and sensors to produce a length of the smart yarn; and
winding the length of the smart yarn onto a second bobbin.

6. The method of claim 1:
wherein advancing the set of wires into the assembly field comprises advancing the first wire and the second wire, each comprising an electrically-conductive core and an insulative coating, into the assembly field;
wherein depositing the first volume of solder paste onto the first terminal location comprises depositing the first volume of solder paste over the insulative coating on the first wire at the first terminal location;
wherein depositing the second volume of solder paste onto the second terminal location comprises depositing the second volume of solder paste over the insulative coating on the second wire at the second terminal location; and
wherein heating the set of wires within the assembly field comprises:
heating the first volume of solder paste to burn the insulative coating off of the first wire at the first terminal location and to bond the first volume of solder paste to the electrically-conductive core of the first wire at the first terminal location; and
heating the second volume of solder paste to burn the insulative coating off of the second wire at the second terminal location and to bond the second volume of solder paste to the electrically-conductive core of the second wire at the second terminal location.

7. The method of claim 1, further comprising, for each sensor site along the set of wires, depositing a packing material over the sensor, the first terminal location on the first wire, and the second terminal location on the second wire.

8. The method of claim 7, wherein advancing the set of wires into the assembly field, depositing the first volume of solder paste, depositing the second volume of solder paste, placing the sensor onto the set of wires, heating the set of wires, and depositing the packing material comprise:
advancing the set of wires forward to locate a first sensor site on the set of wires in the assembly field;
depositing the first volume of solder paste onto a first terminal location at the first sensor site on the first wire;
depositing a second volume of solder paste onto a second terminal location at the first sensor site on the second wire;
placing a first sensor onto the set of wires at the first sensor site;
heating the set of wires proximal the first sensor site to bond the first sensor to the set of wires at the first sensor site;
depositing a first volume of packing material comprising a curable resin around the first sensor; and
in response to the first volume of packing material curing, advancing the set of wires forward to locate a second sensor site on the set of wires in the assembly field, the second sensor site offset behind the first sensor site by the sensor offset distance.

9. The method of claim 7:
wherein advancing the set of wires into the assembly field comprises advancing the set of wires and a packing fiber into the assembly field, the packing fiber parallel to the set of wires within the assembly field;
wherein depositing the packing material over the sensor, the first terminal location on the first wire, and the second terminal location on the second wire comprises depositing the packing material over the sensor, the first terminal location, the second terminal location, and an adjacent segment of the packing fiber to intermittently bond the packing fiber to the set of wires; and
wherein wrapping fibers around the set of wires and sensors comprises wrapping fibers around the set of wires, sensors, and the packing fiber.

10. The method of claim 1, further comprising:
arranging a packing fiber longitudinally along the set of wires; and
radially twisting the packing fiber and the set of wires;
wherein wrapping fibers around the set of wires and sensors comprises wrapping fibers radially about the set of wires, sensors, and the packing fiber.

11. The method of claim 1, wherein depositing the first volume of solder paste onto the first terminal location on the first wire and depositing the second volume of solder paste onto the second terminal location on the second wire comprise:
aligning a solder mask over the set of wires within the assembly field, the solder mask defining a set of perforations patterned according to a terminal arrangement of the sensors; and
spraying solder paste through the set of perforations in the solder mask and onto the set of wires.

12. The method of claim 1:
wherein advancing the set of wires into the assembly field comprises tensioning the set of wires to draw a first sensor site, in the series of sensor sites along the set of wires, into the assembly field;

wherein heating the set of wires to reflow the first volume of solder paste and the second volume of solder paste comprises:
  reducing tension on the set of wires across the first sensor site in preparation for heating the set of wires;
  heating the set of wires to reflow the first volume of solder paste and the second volume of solder paste; and
  in response to the set of wires at the first sensor site cooling to below a threshold temperature, increasing tension on the set of wires to draw the first sensor site out of the assembly field.

13. The method of claim 1, wherein advancing the set of wires into the assembly field, depositing the first volume of solder paste, depositing the second volume of solder paste, placing the sensor onto the set of wires, and heating the set of wires comprise sequentially:
  advancing the set of wires forward to locate a first sensor site on the set of wires over a fixed assembly surface within the assembly field;
  constraining the set of wires relative to the fixed assembly surface;
  advancing a solder paste module into position over the first sensor site to deposit the first volume of solder paste onto the first wire and to deposit the second volume of solder paste onto the second wire;
  advancing a component placement module into position over the first sensor site to place a first sensor onto the set of wires at the first sensor site;
  advancing a reflow module into position over the first sensor site to heat the set of wires proximal the first sensor site;
  releasing the set of wires from the fixed assembly surface; and
  advancing the set of wires forward to locate a second sensor site on the set of wires over the fixed assembly surface, the second sensor site offset behind the first sensor site by the sensor offset distance.

14. The method of claim 1, wherein advancing the set of wires into the assembly field comprises:
  advancing the set of wires forward to locate a first sensor site on the set of wires over an assembly surface within the assembly field;
  triggering a first clamp and a second clamp to bind the set of wires against the assembly surface, the first clamp arranged across an entry side of the assembly surface, the second clamp arranged across an exit side of the assembly surface,
  in response to assembly of a first sensor onto the first sensor site on the set of wires:
    triggering the first clamp and the second clamp to release the set of wires from the assembly surface; and
    advancing the set of wires forward to locate a second sensor site on the set of wires over the assembly surface, the second sensor site offset behind the first sensor site by an integer multiple of the sensor offset distance.

15. The method of claim 14:
  wherein depositing the first volume of solder paste, depositing the second volume of solder paste, placing the sensor onto the set of wires, and heating the set of wires comprise sequentially advancing the assembly surface, clamped to the set of wires and spanning the first sensor site, from a solder paste module to a component placement module to a reflow module; and
  wherein advancing the set of wires forward to locate the second sensor site on the set of wires over the assembly surface comprises retracting the assembly surface to locate the second sensor site of the set of wires over the assembly surface.

16. The method of claim 1:
  wherein advancing the set of wires into the assembly field comprises advancing the set of wires comprising a third wire parallel and laterally offset from the second wire opposite the first wire by the wire offset distance within the assembly field;
  further comprising at each sensor site in the series of sensor sites entering the assembly field:
    depositing a third volume of solder paste onto a third terminal location, on the third wire, coincident the sensor site;
    depositing a fourth volume of solder paste onto a fourth terminal location, adjacent the second terminal location on the second wire, coincident the sensor site;
    placing an electrical component onto the set of wires at the sensor site, the electrical component comprising a third terminal in contact with the third volume of solder paste on the third wire and comprising a fourth terminal offset from the third terminal by the terminal offset distance and in contact with the fourth volume of solder paste on the second wire; and
  wherein heating the set of wires within the assembly field comprises heating the set of wires within the assembly field to further reflow the third volume of solder paste and the fourth volume of solder paste.

17. The method of claim 16, further comprising:
  wherein placing the electrical component onto the set of wires at the sensor site comprises placing an electrical component comprising a light element onto the second wire and the third wire at each sensor site in the series of sensor sites along the set of wires;
  wherein wrapping fibers around the set of wires and sensors comprises wrapping fibers around the set of wires and sensors to form the smart yarn;
  knitting a first segment of the smart yarn into a garment;
  connecting a segment of the second wire in the first segment of the smart yarn to a power supply and connecting a segment of the third wire in the first segment of the smart yarn to a ground terminal to illuminate a first light element in the first segment of the smart yarn; and
  determining a location of a first temperature sensor, contained in the first segment of the smart yarn, in the garment based on a location of the first light element in the garment when illuminated.

18. The method of claim 1, wherein heating the set of wires within the assembly field comprises, for each component site in the series of sensor sites along the set of wires:
  locating an insulated volume over the component site; and
  selectively projecting an energy beam onto the first volume of solder paste and the second volume of solder paste to reflow the first volume of solder paste and the second volume of solder paste.

19. A method for producing a smart yarn, the method comprising:
  advancing a set of wires into an assembly field along a longitudinal direction, the set of wires comprising a first wire parallel and laterally offset from a second wire by a wire offset distance approximating a terminal offset distance;
  at each sensor site in a series of sensor sites longitudinally offset along the set of wires extending in the longitudinal direction by a sensor offset distance and sequentially entering the assembly field as the set of wires is advanced into the assembly field:

depositing a first volume of solder paste onto a first terminal location, on the first wire, coincident the sensor site;

depositing a second volume of solder paste onto a second terminal location, on the second wire, coincident the sensor site;

placing a sensor onto the set of wires at the sensor site, the sensor comprising a first terminal in contact with the first volume of solder paste on the first wire and comprising a second terminal offset from the first terminal by the terminal offset distance and in contact with the second volume of solder paste on the second wire; and heating the set of wires within the assembly field to reflow the first volume of solder paste and the second volume of solder paste; and wrapping fibers around the set of wires and sensors arranged along the set of wires to form a continuous length of the smart yarn;

separating a first segment of the smart yarn from the continuous length of the smart yarn; and weaving the first segment of the smart yarn into a garment.

20. The method of claim 19:

wherein separating the first segment of the smart yarn from the continuous length of the smart yarn comprises separating the first segment of the smart yarn from the continuous length of the smart yarn comprising a first sensor coupled to a first segment of the first wire and to a first segment of the second wire;

further comprising knitting a length of a second yarn into the garment comprising a sock, the second yarn excluding wires and sensors;

wherein weaving the segment of the smart yarn into a garment comprises interweaving the first segment of the smart yarn into the sock with a first end of the first segment of the smart yarn terminating proximal a controller junction at an opening of the sock and with the first sensor in the first segment of the smart yarn located in a sole of the sock; and further comprising:

separating a second segment of the smart yarn from the continuous length of the smart yarn, the second segment of the smart yarn comprising a second sensor coupled to a second segment of the first wire and to a second segment of the second wire; and interweaving the second segment of the smart yarn into the sock with a first end of the second segment of the smart yarn terminating proximal the controller junction and with the second sensor in the second segment of the smart yarn offset from the first sensor in the sole of the sock.

* * * * *